(12) United States Patent
Koike et al.

(10) Patent No.: US 8,016,847 B2
(45) Date of Patent: Sep. 13, 2011

(54) LANCET AND LANCING APPARATUS

(75) Inventors: Masufumi Koike, Kyoto (JP); Masahiro Fukuzawa, Kyoto (JP)

(73) Assignee: Arkray, Inc. (JP)

( * ) Notice: Subject to any disclaimer, the term of this patent is extended or adjusted under 35 U.S.C. 154(b) by 1295 days.

(21) Appl. No.: 10/483,206

(22) PCT Filed: Jul. 10, 2002

(86) PCT No.: PCT/JP02/07030
§ 371 (c)(1),
(2), (4) Date: Jan. 7, 2004

(87) PCT Pub. No.: WO03/005907
PCT Pub. Date: Jan. 23, 2003

(65) Prior Publication Data
US 2004/0243165 A1    Dec. 2, 2004

(30) Foreign Application Priority Data
Jul. 11, 2001 (JP) ................... 2001-211332

(51) Int. Cl.
*A61B 17/32* (2006.01)
*A61B 17/34* (2006.01)
(52) U.S. Cl. .................................. 606/181
(58) Field of Classification Search ............. 606/167, 606/181–186; 600/583
See application file for complete search history.

(56) References Cited

U.S. PATENT DOCUMENTS

| | | | | |
|---|---|---|---|---|
| 2,704,072 A | * | 3/1955 | Sarnoff ........................ | 604/138 |
| 2,832,339 A | * | 4/1958 | Sarnoff et al. ................ | 604/138 |
| 3,612,051 A | * | 10/1971 | Arce ............................. | 604/157 |
| 4,388,925 A | * | 6/1983 | Burns ........................... | 606/182 |
| 4,653,513 A | * | 3/1987 | Dombrowski ................. | 600/578 |
| 4,817,603 A | * | 4/1989 | Turner et al. .................. | 606/182 |
| RE32,922 E | | 5/1989 | Levin et al. | |
| 4,889,117 A | | 12/1989 | Stevens | |
| 4,895,147 A | | 1/1990 | Bodicky et al. | |
| 4,990,154 A | | 2/1991 | Brown et al. | |
| 5,074,872 A | * | 12/1991 | Brown et al. ................. | 606/182 |
| 5,100,427 A | * | 3/1992 | Crossman et al. ........... | 606/182 |
| 5,282,822 A | | 2/1994 | Macors et al. | |
| 5,314,442 A | * | 5/1994 | Morita .......................... | 606/182 |
| 5,318,581 A | | 6/1994 | Sunmo | |

(Continued)

FOREIGN PATENT DOCUMENTS

CN    1130282    9/1996

(Continued)

*Primary Examiner* — Darwin P Erezo
*Assistant Examiner* — Dianne Dornbusch
(74) *Attorney, Agent, or Firm* — Studebaker & Brackett PC; Donald R. Studebaker

(57) ABSTRACT

The present invention provides a lancet (X1) which includes a case (1) including an internal space (10), and a lancing unit (2) which includes a lancing needle (20) and which is movable within the internal space (10) in an advancing direction from a wait position to an advanced position. The case (1) includes a main body (11) accommodating the lancing unit (2), and a cap (12) which is molded integral with the main body (11) and detachable from the main body (11). The lancing unit (2) includes a cover portion (22) for covering a portion of the lancing needle (20) on the advancing side, for example. The cover portion (22) is detachable together with the cap (12) by exerting a rotational force for rotating the cap (12) and a pulling force for causing relative movement of the cap (12) in the advancing direction for exposing a front end of the lancing needle (20).

22 Claims, 19 Drawing Sheets

U.S. PATENT DOCUMENTS

| | | | |
|---|---|---|---|
| 5,318,584 A | | 6/1994 | Lange et al. |
| 5,324,302 A | | 6/1994 | Crouse |
| 5,350,392 A | * | 9/1994 | Purcell et al. .................. 606/182 |
| 5,366,469 A | | 11/1994 | Steg et al. |
| 5,421,347 A | | 6/1995 | Enstrom |
| 5,454,828 A | | 10/1995 | Schraga |
| 5,487,748 A | * | 1/1996 | Marshall et al. .............. 606/182 |
| 5,540,709 A | * | 7/1996 | Ramel ........................... 606/183 |
| 5,545,174 A | * | 8/1996 | Schenk et al. ................. 606/182 |
| 5,554,166 A | * | 9/1996 | Lange et al. ................... 606/182 |
| 5,569,287 A | * | 10/1996 | Tezuka et al. ................. 606/182 |
| 5,571,132 A | * | 11/1996 | Mawhirt et al. .............. 606/182 |
| 5,628,764 A | * | 5/1997 | Schraga ........................ 606/182 |
| 5,686,225 A | | 11/1997 | Chang |
| 5,707,384 A | * | 1/1998 | Kim ............................... 606/181 |
| 5,741,288 A | * | 4/1998 | Rife ............................... 606/181 |
| 5,755,733 A | | 5/1998 | Morita |
| 5,871,494 A | * | 2/1999 | Simons et al. ................ 606/181 |
| 5,954,738 A | | 9/1999 | LeVaughn et al. |
| 5,971,941 A | | 10/1999 | Simons et al. |
| 6,024,727 A | | 2/2000 | Thorne et al. |
| 6,045,534 A | | 4/2000 | Jacobbsen et al. |
| 6,056,765 A | | 5/2000 | Bajaj et al. |
| 6,168,606 B1 | | 1/2001 | Levin et al. |
| 6,183,489 B1 | | 2/2001 | Douglas et al. |
| 6,190,398 B1 | | 2/2001 | Schraga |
| 6,248,120 B1 | | 6/2001 | Wyszogrodzki |
| 6,258,112 B1 | | 7/2001 | Schraga |
| 6,315,738 B1 | | 11/2001 | Nishikawa et al. |
| 6,540,762 B1 | | 4/2003 | Bertling |
| 6,540,763 B2 | * | 4/2003 | Teo et al. ...................... 606/182 |
| 6,558,402 B1 | | 5/2003 | Chelak et al. |
| 6,602,268 B2 | | 8/2003 | Kuhr et al. |
| 6,790,199 B1 | | 9/2004 | Gianakos |
| 2002/0087180 A1 | | 7/2002 | Searle et al. |

FOREIGN PATENT DOCUMENTS

| | | |
|---|---|---|
| DE | 43 20 463 | 6/1993 |
| EP | 0 565 819 | 10/1993 |
| EP | 0 838 195 | 4/1998 |
| EP | 0 885 590 | 12/1998 |
| EP | 1 031 319 | 8/2000 |
| EP | 1 060 707 | 12/2000 |
| JP | 5-88503 | 12/1993 |
| JP | 2000-175889 | 6/2000 |
| WO | WO 93/19671 | 10/1993 |
| WO | WO 98/58584 | 12/1998 |
| WO | WO 00/02482 | 1/2000 |

\* cited by examiner

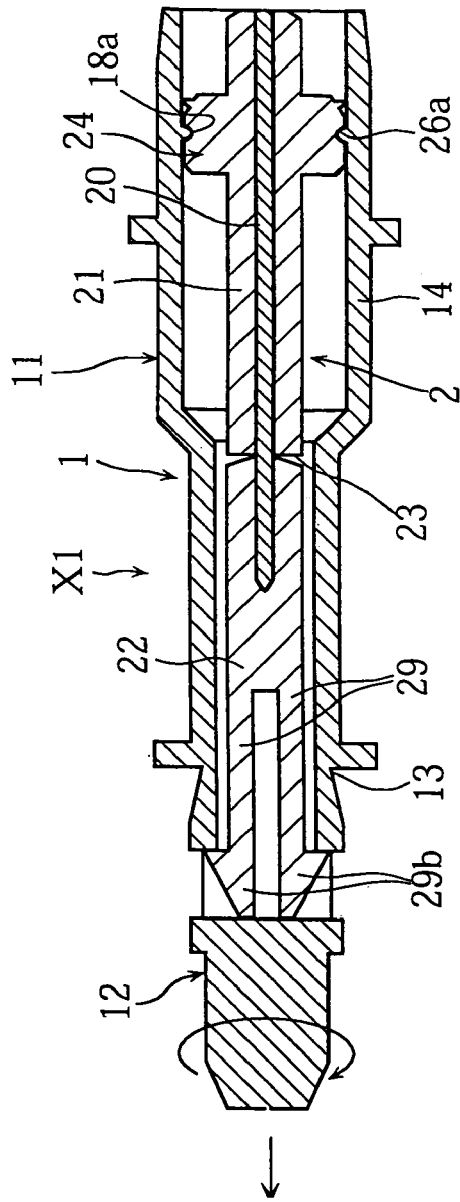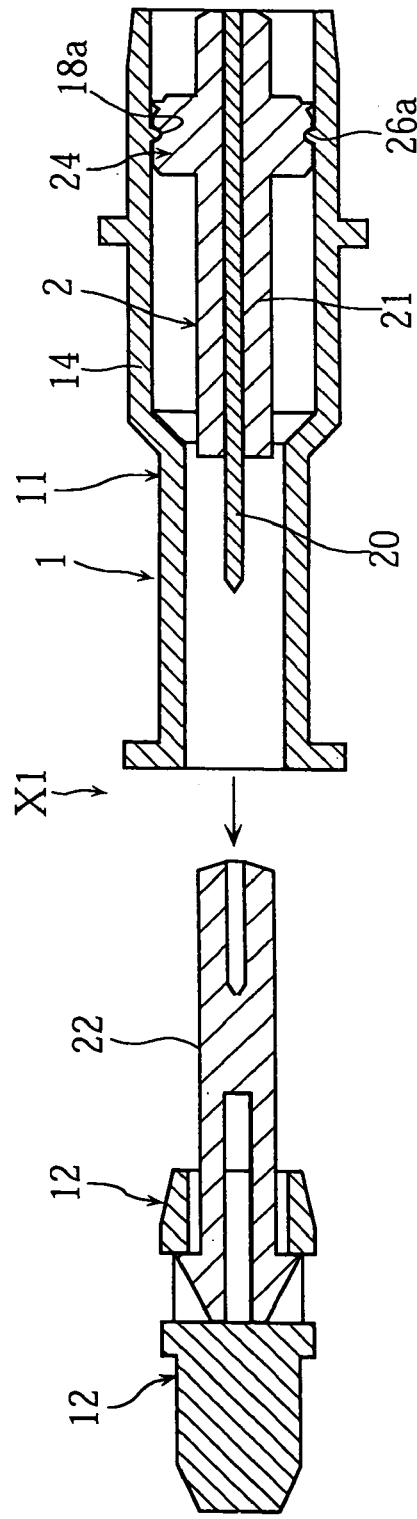

FIG. 16
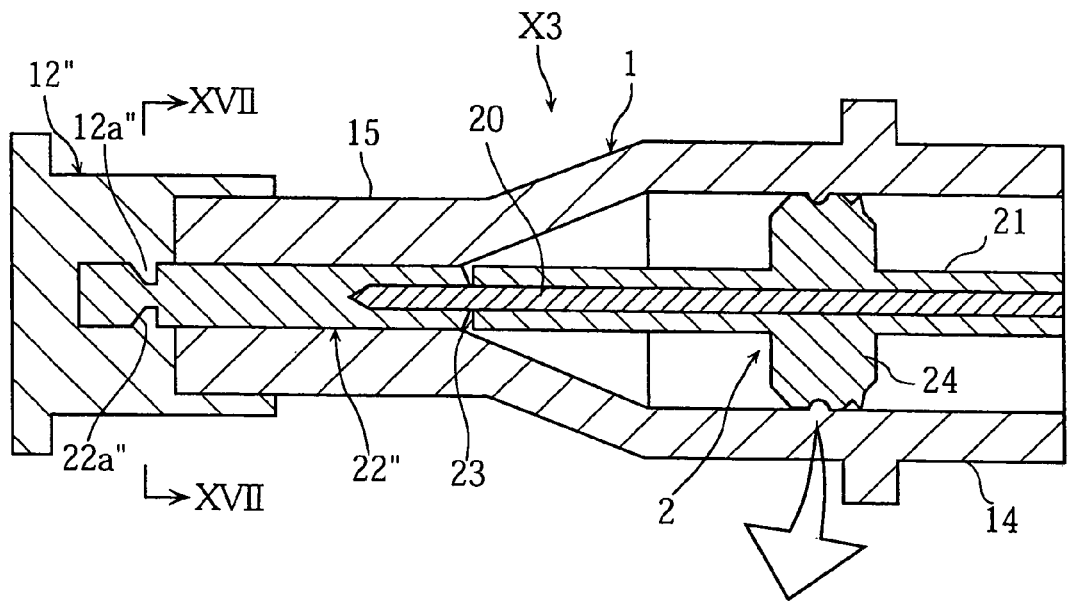
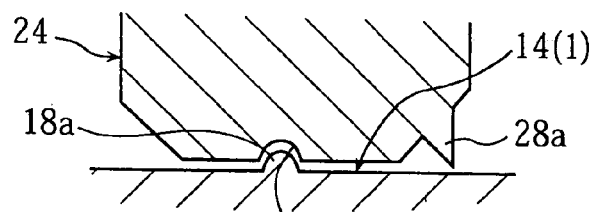
FIG. 17
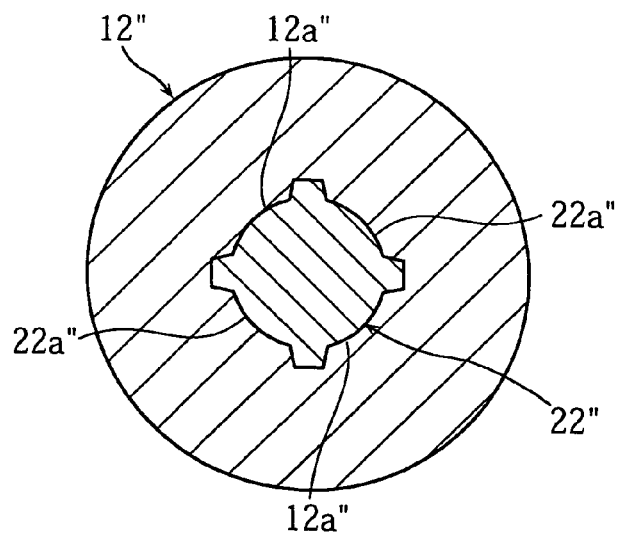

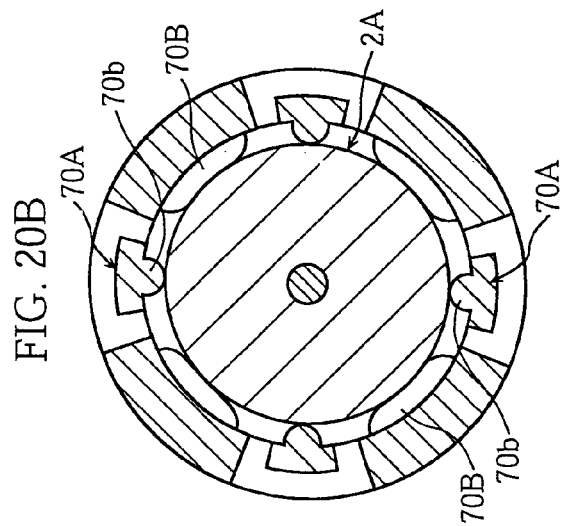
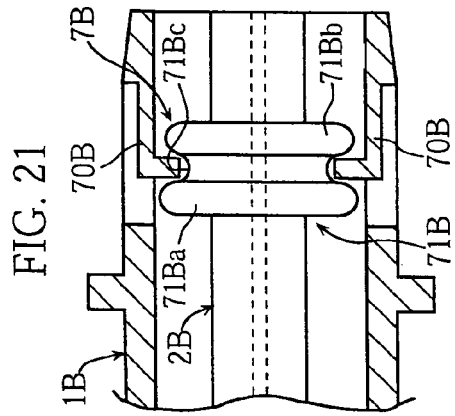
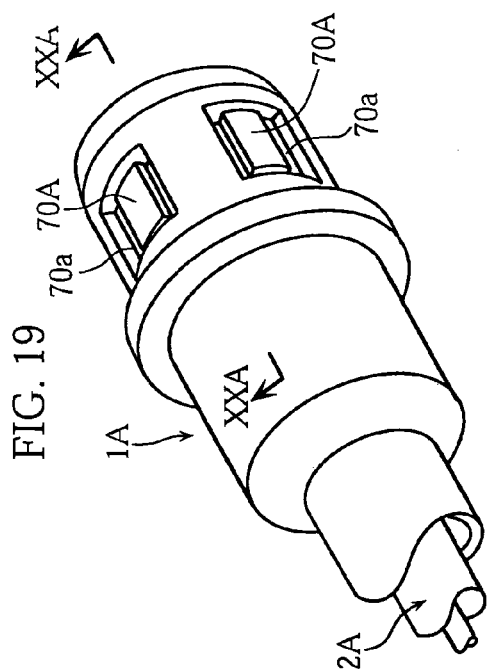
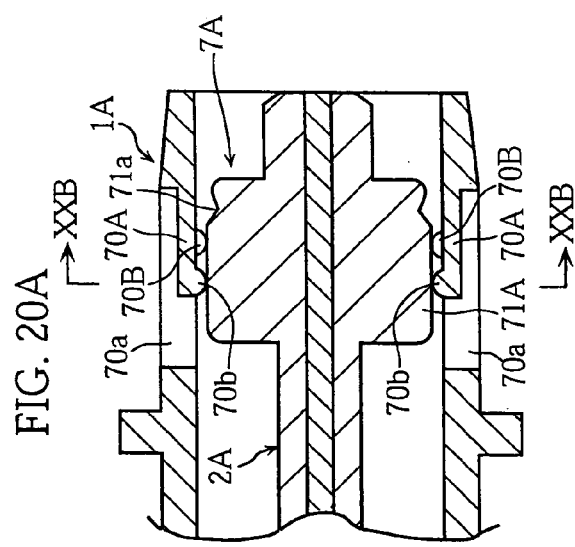

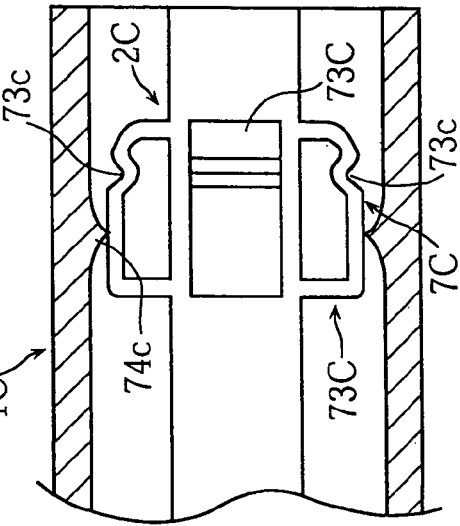
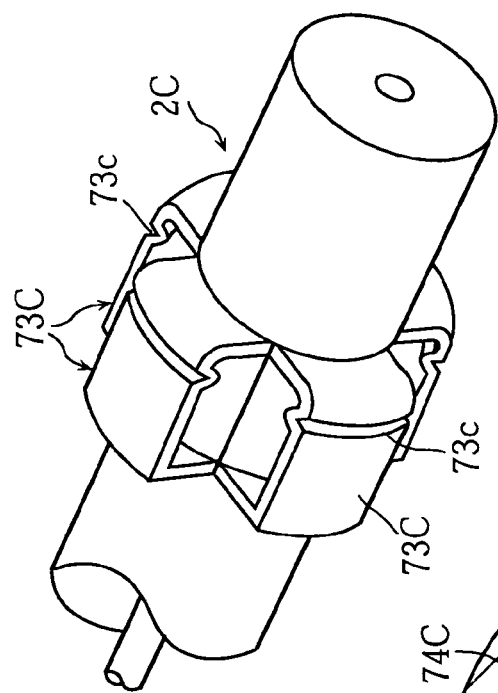
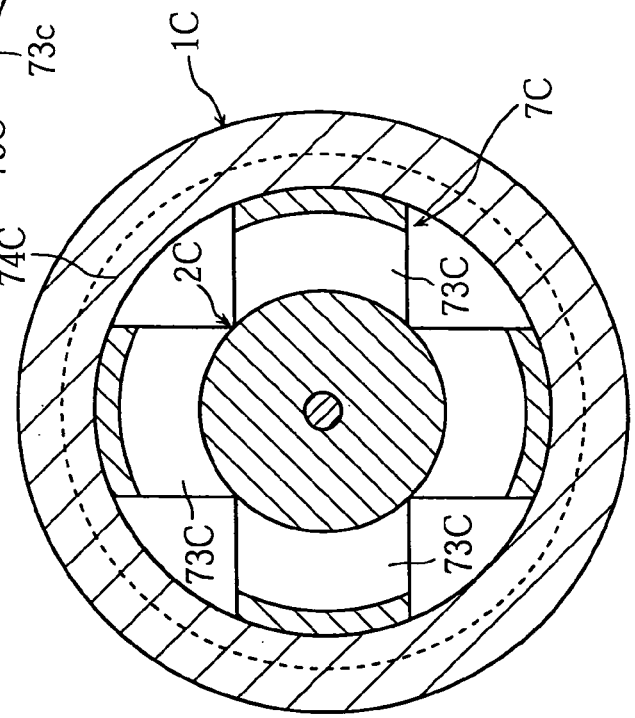

LANCET AND LANCING APPARATUS

TECHNICAL FIELD

The present invention relates to a lancet and a lancing apparatus used to extract body fluid through skin for measuring e.g. the concentration of a target substance contained in the body fluid.

BACKGROUND ART

A portable blood glucose level measuring device has been put to practical use for checking the blood glucose level by an individual who stays at home or away from home. To measure the blood glucose level using such a measuring device, a biosensor may be set to the measuring device for providing an enzyme reaction field, to which blood is supplied. In doing this, a lancing apparatus having a skin-lancing needle may be used for facilitating the bleeding from the skin. From a sanitary point of view, the skin-lancing needle is provided as a disposable lancet. An example of lancet is disclosed in the gazette of JP-U-5-88503. The lancet disclosed in the gazette, suitable for reducing the manufacturing cost due to the reduced number of parts, has a structure shown in FIGS. 27A and 28A of the present application.

The lancet 8 of FIG. 27A includes a needle hub 82 supported by a housing 80 via a breakable portion 81. The needle hub 82 holds a lancing needle 83. The housing 80 is formed with a first opening 80a for allowing access to the rear end 82a of the needle hub 82 to push it, and with a second opening 80b for allowing the projection of the lancing needle 81. At the second opening 80b, a cap 84 is provided for closure. The cap 84 includes a breakable portion 84a so that the front portion 84b of the cap 84 can be removed, as shown in FIG. 27B. The front portion 84b of the cap 84 includes a needle tip accommodation space 84c.

In using the lancet 8, the front portion 84b of the cap 84 is removed, and then the rear end 82a of the needle hub 82 is fitted to a pushing member 85 of the lancing apparatus not shown in the figure. By operating the pushing member 85, the breakable portion 81 is broken, thereby permitting the needle hub 82 to move in the pushing direction (the direction indicated by the arrow A in FIG. 27). As a result, the tip of the lancing needle 83 projects forward from the second opening 80b, so that the lancing needle 83 can lance the skin. After the lancing is finished, the front portion 84b of the cap 84 is turned over, as shown in FIG. 27C, to be attached to the rear portion of the cap 84. Thus, the needle tip is accommodated in the accommodation space 84c.

The lancet 9 shown in FIG. 28A includes a housing 92 in which a needle hub 90 is held via a resilient portion 91. The housing 92 has an opening 92b to which a cap 94 is attached. The cap 94 includes a breakable portion 94a and an accommodation space 94c.

In the lancet 9 again, after the front end 94b of the cap 94 is removed, the front end of a lancing needle 93 is caused to project from the housing 92, as the rear end 90a of the needle hub 90 is pushed in the direction of the illustrated arrow A in FIG. 28B. Then, when the pushing force is removed, the restoring force of the resilient member 91 brings the needle hub 90 back to the initial position, so that the lancing needle 93 is accommodated in the housing 92.

In the lancets 8, 9 shown in FIGS. 27 and 28, the lancing needles 83, 93 are left projecting from the needle hubs 82, 90. Specifically, the lancing needles 83, 93 are embedded in the needle hubs 82, 90 by insert molding except for the front ends. However, in insert molding the lancing needles 83, 93 with the needle tips 83, 93 exposed, care should be taken so as not to bend the needle tips, which makes the manufacture difficult. Further, the needle hubs 82, 90 are formed integral with the housings 80, 90 via the breakable portion 81 or the resilient portion 91, and the molding for such an integral configuration is difficult. Moreover, in attaching the caps 84, 94 to the housing 80, 92 via the breakable portion 81 or the resilient portion 91, care should be taken so as not to bend the needle tips, which causes the operation efficiency to deteriorate. In summary, the lancets 8, 9 shown in FIGS. 27 and 28 are disadvantageous in terms of production cost because of the poor operation efficiency and difficult manufacturing process.

Further, in the lancet 8 shown in FIG. 27, the needle hub 82 and the lancing needle 83 are freely movable relative to the housing 80 after the breakable portion 81 is broken. This allows the lancing needle 83 to project from the housing 80 when the lancet 8 is detached from the lancing apparatus for disposal. Thus, there may be a danger that the lancing needle 83 may stick into a finger, for example.

DISCLOSURE OF THE INVENTION

An object of the present invention is to provide a lancet which can be manufactured advantageously in terms of cost and which can prevent the lancing needle after use from projecting.

According to a first aspect of the present invention, there is provided a lancet comprising: a case including an internal space; and a lancing unit including a lancing needle and movable within the internal space in an advancing direction from a wait position to an advanced position. The case comprises a main body accommodating the lancing unit, and a cap formed integral with the main body, the cap being detachable from the main body.

For example, the lancing unit may comprise: a holder portion for holding a portion of the lancing needle on a retreating side which is opposite to the advancing side; and a cover portion for covering a portion of the lancing needle on the advancing side, the cover portion being detachable from the holder portion. The cover portion is detached together with the cap for exposing a front end of the lancing needle. The cover portion may be molded integral with the holder portion. In that case, the lancing needle may be insert-molded in the cover portion and the holder portion. The cover portion may be formed separately from the holder portion. In that case, the lancing needle is fixed to the holder portion with an adhesive, for example. The lancing needle may be insert-molded in the holder portion.

Preferably, the lancet may further comprise rotational means for rotating the cover portion in accordance with rotation of the cap. The cover portion is detached together with the cap by exerting a rotational force for rotating the cap and a pulling force for causing relative movement of the cap in the advancing direction.

The rotational means may comprise: an engagement piece which is provided on the cover portion and has a front end movable in a direction transverse to the advancing direction of the lancing unit; and an engagement hole provided at the cap for engagement with the engagement piece for restraining the front end of the engagement piece in the rotational direction and in the advancing direction.

The rotational means may comprise a recess or a projection provided on the cover portion, and a projection or a recess provided on the cap for engagement with the recess or the projection of the cover portion.

Preferably, the lancet may further comprise rotation preventing means for preventing the holder portion from rotating when the cap is rotated.

Preferably, the lancet may further comprise wait position holding means for holding the lancing unit at the wait position. The wait position holding means may include a resilient portion provided on at least one of the case and the lancing unit, the lancing unit being held in place by a spring force of the resilient portion.

Preferably, the lancet may further comprise retreated position holding means for holding the lancing unit at a retreated position after the lancing unit is advanced from the wait position to the advanced position and then retreated from the advanced position to the retreated position.

According to a second aspect of the present invention, there is provided a lancet comprising: a case including an internal space; and a lancing unit including a lancing needle and movable within the internal space in an advancing direction from a wait position to an advanced position. The case may comprise: a main body which accommodates the lancing unit and has an opening for allowing the lancing needle to advance there through; and a cap which covers the opening and is detachable from the main body. The lancing unit may comprise: a holder portion for holding a portion of the lancing needle on a retreating side; and a cover portion for covering a portion of the lancing needle on the advancing side, the cover portion being detachable from the holder portion. The cover portion may be detached together with the cap for exposing a front end of the lancing needle, without causing the lancing needle to project from the opening.

The cover portion may be molded integral with the holder portion. In that case, the lancing needle may be insert-molded in the cover portion and the holder portion. The cover portion may be formed separately from the holder portion. In that case, the lancing needle is fixed to the holder portion with an adhesive, for example. The lancing needle may be insert-molded in the holder portion.

Preferably, the lancet may further comprise rotational means for rotating the cover portion in accordance with rotation of the cap. The cover portion may be detached together with the cap by exerting a rotational force for rotating the cap and a pulling force for causing relative movement of the cap in the advancing direction.

The rotational means may comprise: an engagement piece provided at the cover portion and having a front end movable in a direction transverse to the advancing direction of the lancing unit; and an engagement hole provided at the cap for engagement with the engagement piece for restraining the front end of the engagement piece in the rotational direction and the advancing direction.

The rotational means may comprise: a recess or a projection provided at the cover portion; and a projection or a recess provided at the cap for engagement with the recess or the projection of the cover portion.

Preferably, there may be provided a weak portion at a boundary between the cap and the main body. In this case, the cap can be easily separated from the main body. The weak portion may be provided by forming a notch at the boundary, or making the boundary thinner than other portions, or by forming a plurality of through-holes communicating with the internal space at the boundary.

Preferably, there may be provided a weak portion at a boundary between the holder portion and the cover portion. In this case, the cover portion can be easily separated from the holder portion. The weak portion may be provided by forming a notch or by making the boundary thinner than other portions.

Preferably, the lancet may further comprise rotation preventing means for preventing the holder portion from rotating when the cap is rotated.

According to a first aspect of the present invention, there may be provided a lancet comprising: a case including an internal space; a lancing unit including a lancing needle and movable within the internal space in an advancing direction from a wait position to an advanced position; and wait position holding means for holding the lancing unit at the wait position. The wait position holding means includes a resilient portion provided at least at one of the case and the lancing unit for holding the lancing unit in place by resilient force.

Preferably, the lancet may further comprise retreated position holding means for holding the lancing unit at a retreated position after the lancing unit is retreated from the advanced position. The wait position holding means may include a projection provided on an inner surface of the case. The retreated position holding means may include a recess provided at the resilient portion for engagement with the projection of the case.

According to a fourth aspect of the present invention, there may be provided a lancet comprising: a lancing unit including a lancing needle; a case holding the lancing unit movably from a wait position to an advanced position; and retreated position holding means for holding the lancing unit at a retreated position after the lancing unit is retreated from the advanced position.

The retreated position holding means includes a resilient portion provided at least one of the case and the lancing unit for holding the lancing unit by resilient force.

Preferably, the resilient portion may comprise a swayable portion provided on the lancing unit and urged outward of the lancing unit.

Preferably, the lancet may further comprise wait position holding means for holding the lancing unit at the wait position. The wait position holding means may comprise: a recess or a projection provided at an outer surface of the lancing unit; and a projection or a recess formed at an inner surface of the case for engagement with the recess or the projection of the lancing unit. The retreated position holding means may comprise: the projection or the recess of the case; and a recess or a projection provided on the retreating side of the recess or the projection of the lancing unit for engagement with the projection or the recess of the case.

The retreated position holding means may comprise: the projection provided at the inner surface of the case; a first circular flange projecting from the outer surface of the lancing unit; and a second circular flange which is provided adjacent to and on the retreating side of the first circular flange and which is smaller in diameter than the first circular flange. The second circular flange together with the first circular flange may define an engagement groove for engagement with the projection.

According to a fifth aspect of the present invention, there may be provided a lancing apparatus for advancing a lancing needle incorporated in a lancet mounted on the lancing apparatus. The lancet comprising: a lancing unit including a lancing needle; a case holding the lancing unit movably from a wait position to an advanced position; and retreated position holding means for holding the lancing unit at a retreated position after the lancing unit is retreated from the advanced position. The lancing apparatus may comprise a movable member which is movable in an advancing direction and is arranged to hold a retreat-side portion of the lancing unit. The movable member may move in the advancing direction for bringing the lancing unit to the advanced position. The case may be moved in the advancing direction relative to the lancing apparatus to detach the lancet from the lancing apparatus, the detachment being performed while the lancing unit is held at the retreated position by the retreated position holding means after the lancing unit is moved in a retreating direction relative to the case.

BRIEF DESCRIPTION OF THE DRAWINGS

FIGS. 9A and 9B are sectional views for describing how a cap is detached from the lancet shown in FIG. 1.

FIG. 16 is a sectional view of a lancet according to a third embodiment of the present invention, principal portions of which are illustrated as enlarged.

FIG. 17 is a sectional view taken along lines XVII-XVII in FIG. 16.

FIG. 19 is a perspective view showing a principal portion of a lancet according to a fifth embodiment of the present invention.

FIG. 20A is a sectional view taken along lines XXA-XXA in FIG. 19, whereas FIG. 20B is a sectional view taken along lines XXB-XXB in FIG. 20A.

FIG. 21 is a perspective sectional view showing a principal portion of a lancet according to a sixth embodiment of the present invention.

FIG. 22 is a perspective view showing a principal portion of a lancing unit of a lancet according to a seventh embodiment of the present invention.

FIG. 23 is a sectional view of a lancet for describing wait position holding means.

FIG. 24 is a sectional view of a lancet for describing wait position holding means.

FIGS. 25A through 27C are perspective sectional views of a principal portion of a lancet according to an eighth embodiment of the present invention.

FIGS. 27A through 27C are sectional views illustrating an example of prior art lancet.

BEST MODE FOR CARRYING OUT THE INVENTION

Figure 1:
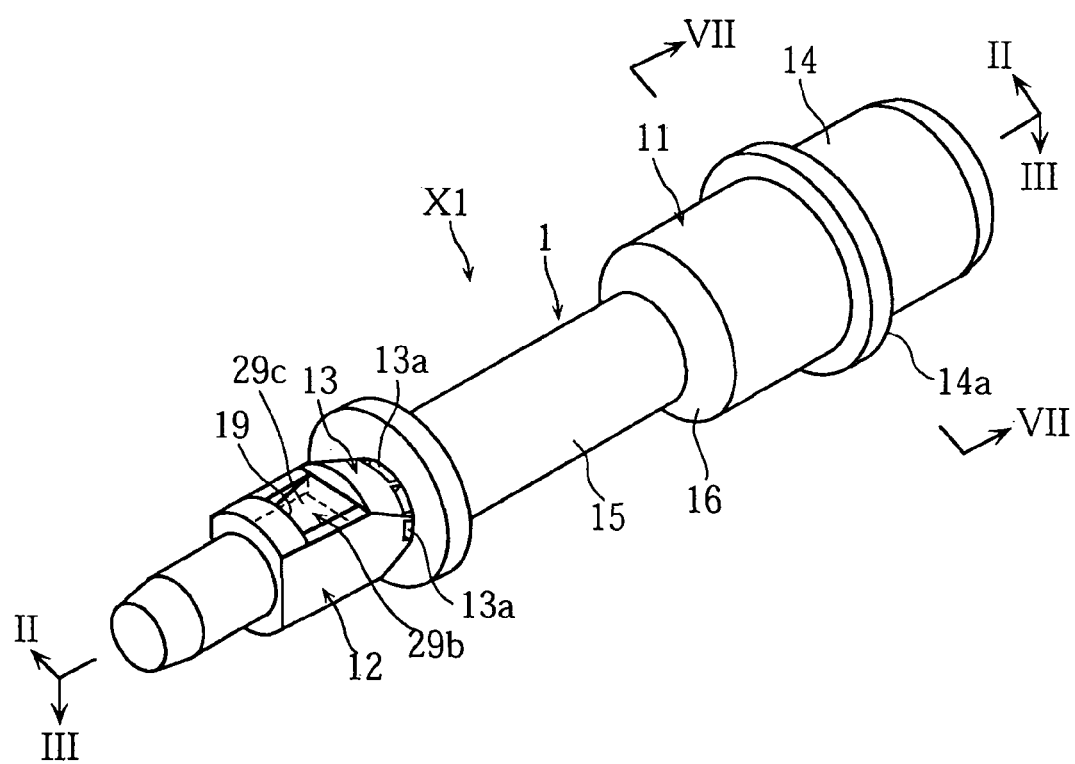
FIG. 1 is a perspective view showing the entirety of a lancet according to a first embodiment of the present invention.

A lancet X1 according to a first embodiment will be described with reference to FIGS. 1 through 3. As shown in the figures, the lancet X1 includes a lancing unit 2 held in a case 1. In use, as will be described later, the lancet X1 is attached to the front end of a lancing apparatus.

The case 1 includes a main body 11 with an internal space 10, and a cap 12 integral with the main body. The internal space 10 accommodates the lancing unit 2, and the lancing unit 2 with a cover portion 22 removed is movable forward and backward within the internal space 10, as will be described later. The internal space 10 communicates with the outside through an opening 10a.

Referring to FIGS. 2 through 5, a weak portion 13 is provided at the boundary between the main body 11 and the cap 12. The weak portion 13, which serves to facilitate the detachment of the cap 12 from the main body 11, is provided by forming a plurality of through-holes 13a, as clearly shown in FIGS. 4 and 5. The number and configuration of the through-holes 13a are not limited. The weak portion may be formed by reducing the thickness at the boundary between the main body and the cap selectively.

Figure 2:
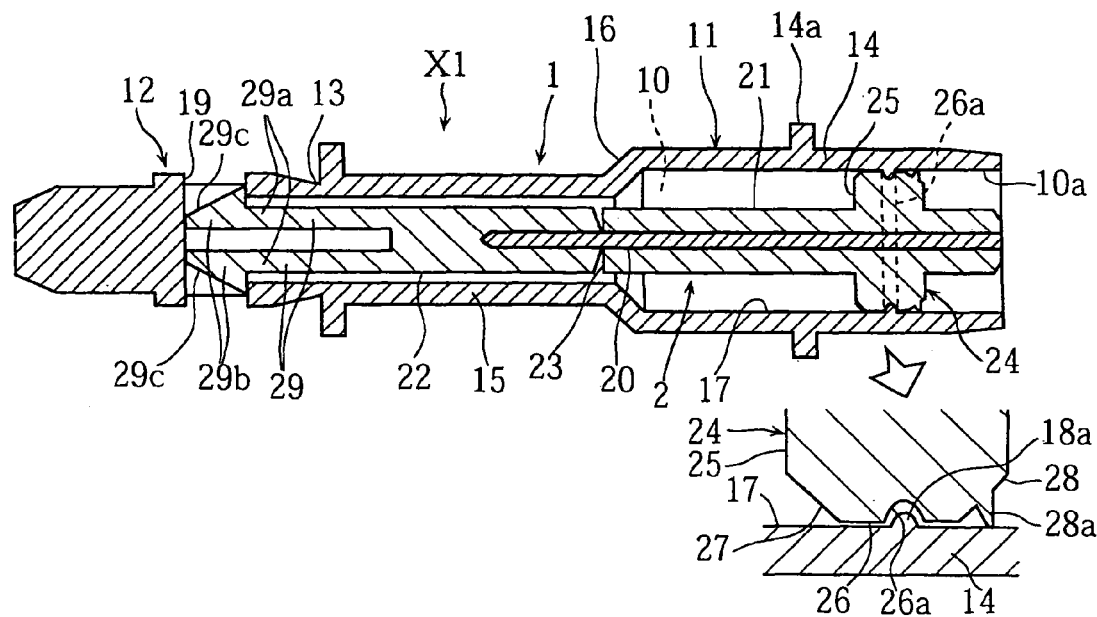
FIG. 2 is a sectional view taken along lines II-II in FIG. 1.
Figure 3:
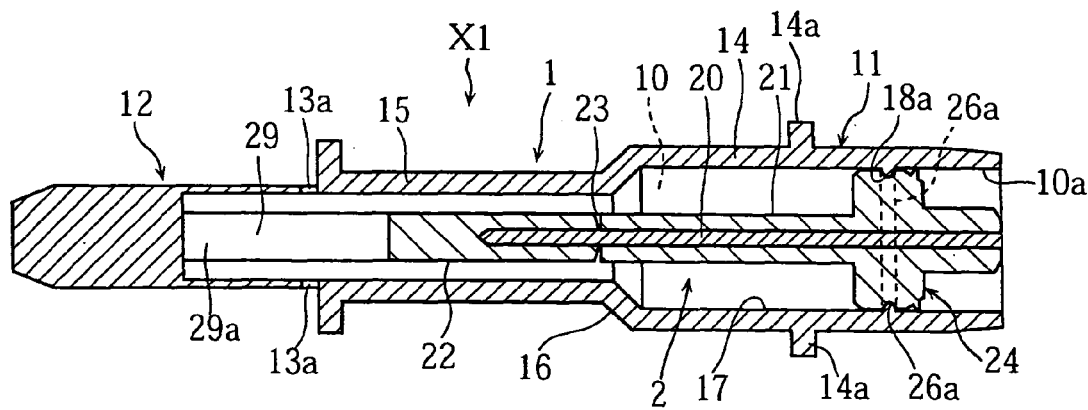
FIG. 3 is a sectional view taken along lines III-III in FIG. 1.
Figure 4:
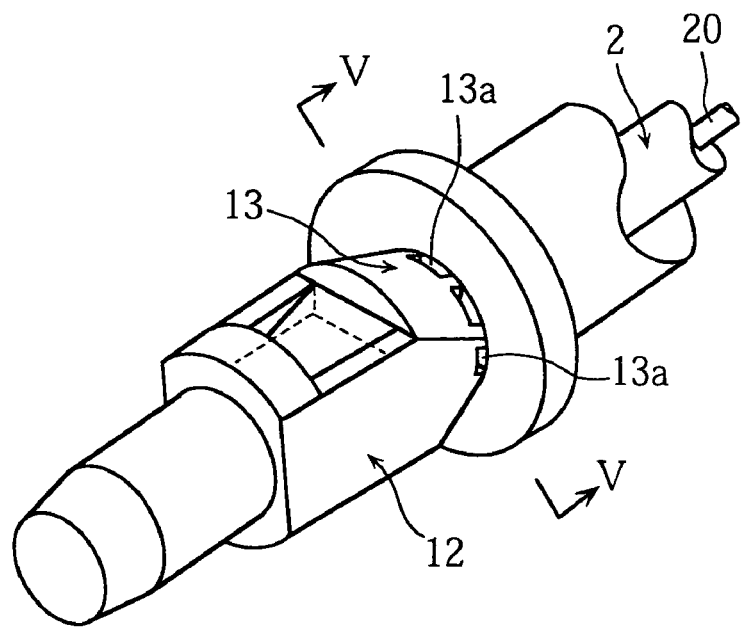
FIG. 4 is an enlarged view of a principal portion for showing a weak portion of a case.
Figure 5:
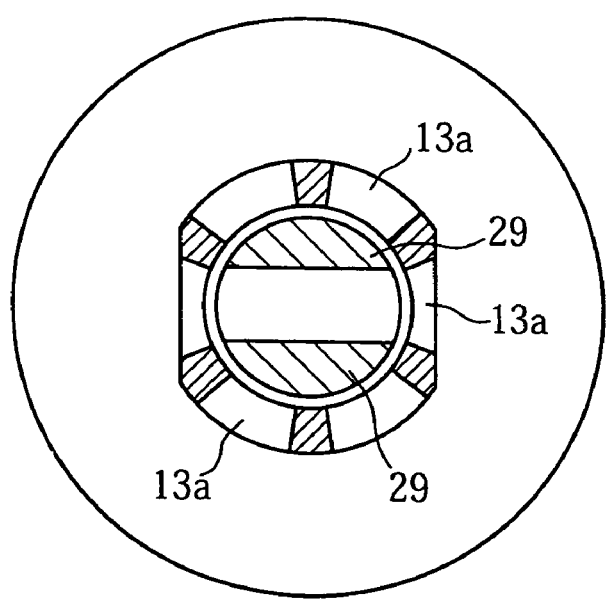
FIG. 5 is a sectional view taken along lines V-V in FIG. 4.
Figure 7:
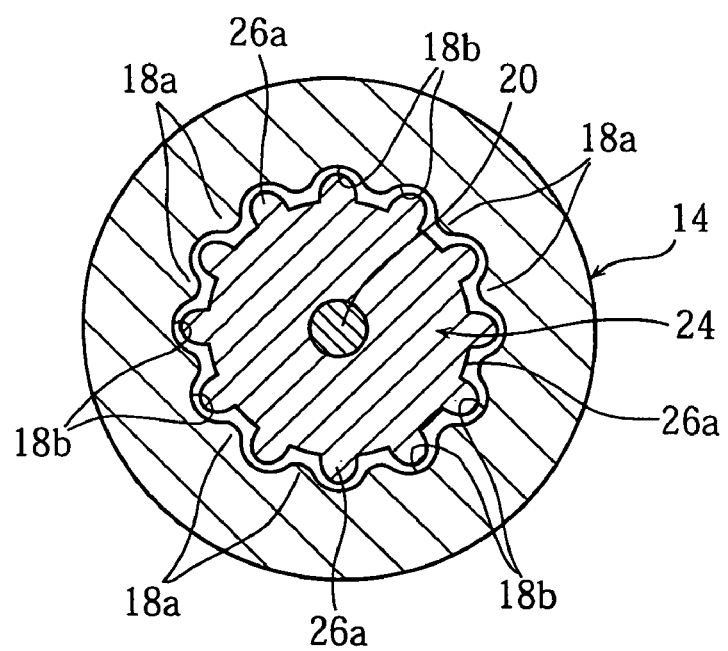
FIG. 7 is a sectional view taken along lines VII-VII in FIG. 1.

As shown in FIGS. 1 through 3, the main body 11, which is cylindrical as a whole, includes a first cylindrical portion 14 having a relatively large inner diameter, a second cylindrical portion 15 having a smaller diameter, and a tapered portion 16 connecting the first cylindrical portion 14 to the second cylindrical portion 15. As shown in FIG. 7, the first cylindrical portion 14 has an inner surface 17 formed with a plurality of projections 18a and recesses 18b. As shown in FIGS. 1 through 3, the first cylindrical portion 14 has an outer surface provided with an annular flange 14a. As will be described later, the flange 14a serves as a stopper in mounting the lancet X1 to the lancing apparatus.

The cap 12 includes two engagement holes 19 communicating with the internal space 10.

The lancing unit 2 includes a lancing needle 20 insert-molded in a holder portion 21 and the cover portion 22. The holder portion 21 and the cover portion 22 are integrally molded and have a boundary which is made weak by a notch 23. The holder portion 21 includes a stopper 24 whose maximum diameter is slightly smaller than the inner diameter of the first cylindrical portion 14. The holder portion 21 and the cover portion 22 need not necessarily be integrally molded but may be formed separately. The lancing needle 20 may be fixed to the holder portion 21 with an adhesive.

Figure 6:
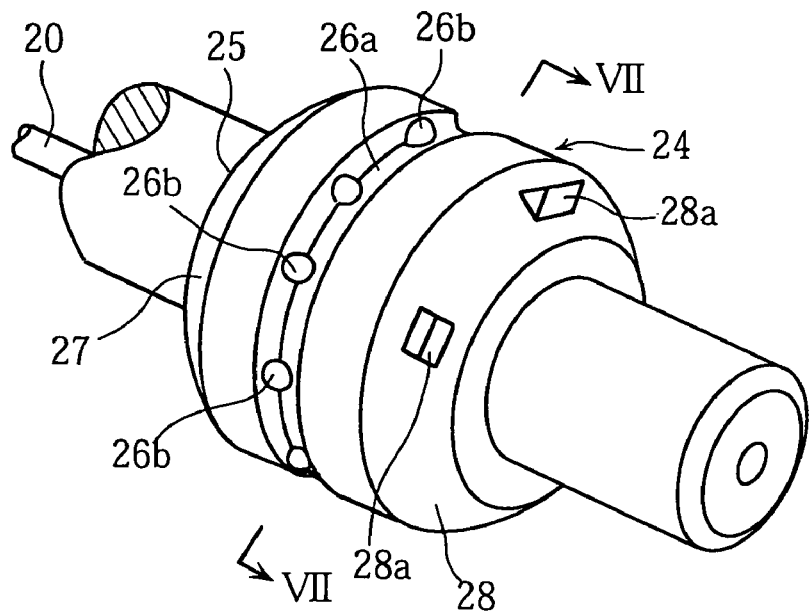
FIG. 6 is an enlarged view of a principal portion for describing wait position holding means.

As clearly shown in FIGS. 2 and 6, the stopper 24 includes a stopper surface 25, a cylindrical surface 26 and tapered surfaces 27 and 28.

When the lancing unit 2, with the cover portion 22 detached, moves in the advancing direction in the internal space 10 (toward the left side in FIGS. 2 and 4), the stopper surface 25 interferes with the tapered portion 16 of the case 1 to inhibit the movement of the lancing unit 2 at the lancing position.

As clearly shown in FIG. 6, the cylindrical surface 26 is formed with an annular recess 26a. The annular recess 26a is provided with a plurality of projections 26b. The annular recess 26a and the projections 26b are provided for engagement with the projections 18a of the first cylindrical portion 14. When these members are engaged with each other, the lancing unit 2 is held at wait position in the case 1, at which the rotation of the lancing unit 2 is inhibited. However, the structure for inhibiting the rotation of the lancing unit 2 is not limited to that shown in FIG. 7. For example, the rotation of the lancing unit 2 relative to the case 1 may be inhibited at a portion of the lancing unit 2 other than the stopper 24. Further, the configuration and number of the projections 26b and the projections 18a may be varied as long as they can inhibit the rotation of the lancing unit 2.

As shown in FIGS. 2 and 6, the tapered surface 28 is provided with a plurality of projections 28a. As will be described later, the projections 28a function to hold the lancing unit 2 at the wait position.

The cover portion 22 covers a tip of the lancing needle 20 to prevent the lancing needle 20 from being exposed to the air. As clearly shown in FIG. 2, the cover portion 22, at an end, has two engagement pieces 29. Each of the engagement pieces 29, which are spaced from each other by a predetermined distance, has a free end 29a, thereby having the ability of spring. Therefore, the ends 29a of the respective engagement pieces 29 are movable toward or away from each other. The end 29a of each engagement piece 29 is provided with a hook 29b having a tapered surface 29c. As clearly shown in FIGS. 1 and 2, the hooks 29b come into engagement with the engagement holes 19 of the cap 12. When the hooks 29b are brought into engagement with the engagement holes 19, the hooks 29b and hence the cover portion 22 are secured to the cap 12 to be unmovable in the rotating direction and the advancing/retreating direction.

Figure 8:
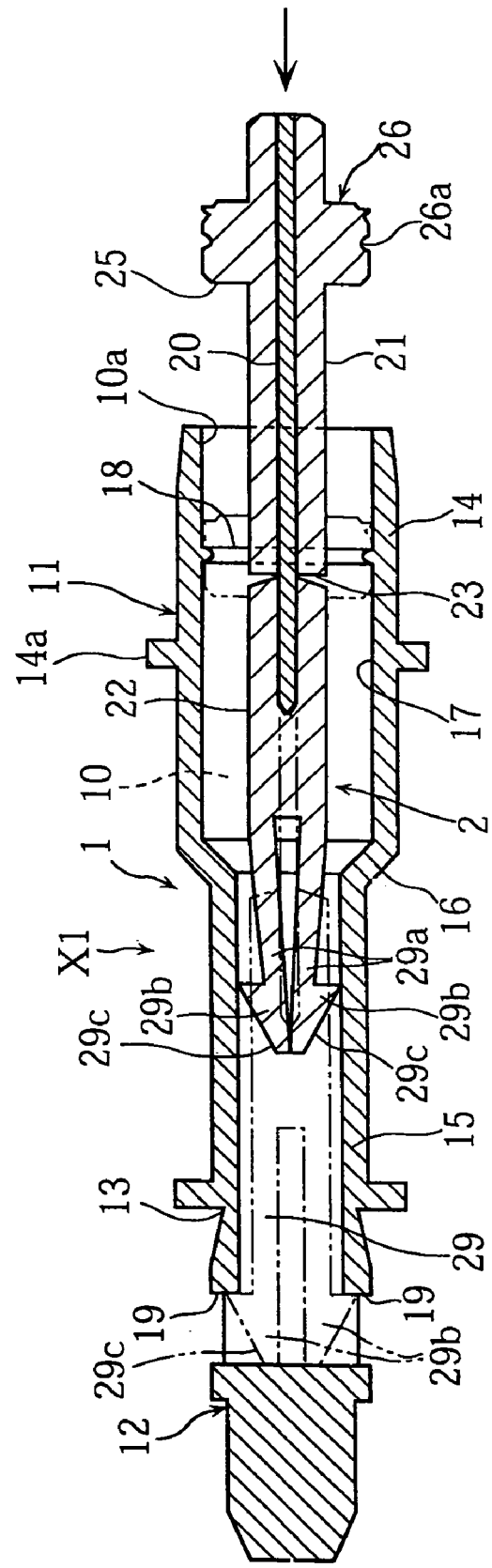
FIG. 8 is a sectional view for describing the process of assembling the lancet shown in FIG. 1.

The above lancet X1 may be prepared by making the case 1 and the lancing unit 2 by resin-molding and then mounting the lancing unit 2 to the case 1. As shown in FIG. 8, the lancing unit 2 can be mounted to the case 1 merely by inserting the lancing unit 2 through the opening 10a of the case 1, with the engagement pieces 29 coming first.

In inserting the lancing unit 2, as the engagement pieces 29 pass through the first cylindrical portion 14 and come closer to the tapered portion 16, the tapered surfaces 29c of the engagement pieces 29 will eventually interfere with the tapered portion 16. When a force in the insertion direction (the direction indicated by the arrow in FIG. 8) is further exerted onto the tapered surfaces 29c, a force acts on the tapered surfaces 29c to bring the paired engagement pieces 29 closer to each other. As a result, the engagement pieces 29 can pass also through the second cylindrical portion 15 having a smaller diameter. When the lancing unit 2 is inserted deeper, the ends 29a of the engagement pieces 29 come close to the engagement holes 19 of the cap 12, and the force acting on the tapered surfaces 29c is released when the hooks 29b correspond in position to the engagement holes 19. At that time, the paired engagement pieces 29 move away from each other to cause the hooks 29b to be engaged in the engagement holes 19. On the other hand, as clearly shown in FIG. 2, the projections 18a of the case 1 come into engagement with the annular recess 26a of the lancing unit 2 to hold the lancing unit 2 at the wait position within the case 1.

Advantageously, the lancet X1 can be assembled easily by inserting the lancing unit 2 into the case 1 after the case 1 and the lancing unit 2 are resin-molded. Further, since the lancing needle 20 is covered with the cover portion 22 while the lancet X1 is being assembled, the assembling work is performed safely, and the needle tip will not be bent. Also, in the case 1, the cap 12 is integrally resin-molded on the main body 11, whereby there is no need to prepare a separate mold for forming the cap 12, which is advantageous in terms of the production cost. Still further, the lancing unit 2 can be made easily by molding the holder portion 21 integrally with the cover portion 22 and insert-molding the lancing needle 20 so as to be entirely embedded in these. Since the needle tip is covered with the cover portion 22, bending of the needle tip in making the lancing unit 2 can be prevented.

As previously noted, the lancet X1 when used is mounted on a lancing apparatus. Before that, however, the cap 12 of the case 1 need be detached. The detachment of the cap 12 can be performed just by exerting a rotational force and a pulling force onto the cap 12, as shown in FIG. 9A.

When the cap 12 is rotated, the boundary between the cap 12 and the main body 11 is broken due to the existence of the weak portion 13. At that time, since the cover portion 22 of the lancing unit 2 is secured to the cap 12 in the rotational direction, the lancing unit 2 tends to turn together with the cap 12. However, the rotation of the lancing unit 2 relative to the first cylindrical portion 14 is inhibited by the stopper 24, while the boundary between the cover portion 22 and the holder portion 21 is made weak by the provision of the notch 23. Therefore, only the cover portion 22 rotates together with the cap 12, and the boundary of the lancing unit 2 is broken.

When a pulling force is exerted on the cap 12, the pulling force also acts on the cover portion 22 of the lancing unit 2, because the cover portion 22 is secured to the cap 12 in the advancing/retreating direction. Since the annular recess 26a of the lancing unit 2 engages the projections 18a, the cover portion 22 is pulled out together with the cap 12 to expose the front end of the lancing needle 20, as shown in FIG. 9B.

Figure 10A:
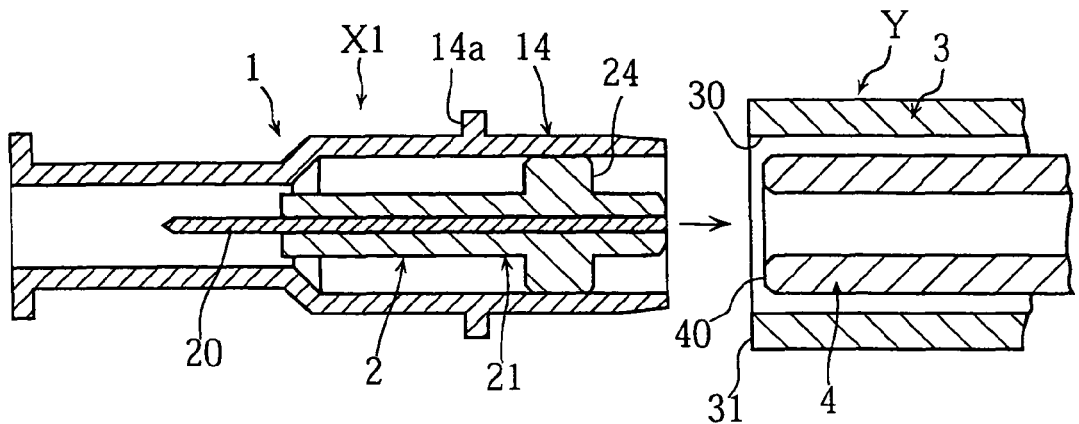
FIGS. 10A through 10C are sectional views for describing the work for mounting the lancet shown in FIG. 1 to a lancing apparatus.

As shown in FIG. 10A, the lancing apparatus Y to which the lancet X1 is mounted includes a housing 3, and a movable member 4 which is movable within the housing 3 in the advancing/retreating direction. The housing 3 has a front end formed with an opening 30 and has an inner diameter corresponding to the outer diameter of the first cylindrical portion 14 of the case 1 of the lancet X1. The movable member 4 has a cylindrical front end having an outer diameter corresponding to the inner diameter of the first cylindrical portion 14, and an inner diameter corresponding to the outer diameter of the rear end of the holder portion 21 of the lancing unit 2.

The lancet X1 is mounted to the lancing apparatus Y by inserting the rear end of the lancet X1 into the front end of the lancing apparatus. Specifically, as shown in FIGS. 10B and 10C, the lancet X1 is mounted to the lancing apparatus Y by fitting the holder portion 21 of the lancing unit 2 into the movable member 4 while fitting the first cylindrical portion 14 of the case 1 between the housing 3 and the movable member 4.

Figure 10B:
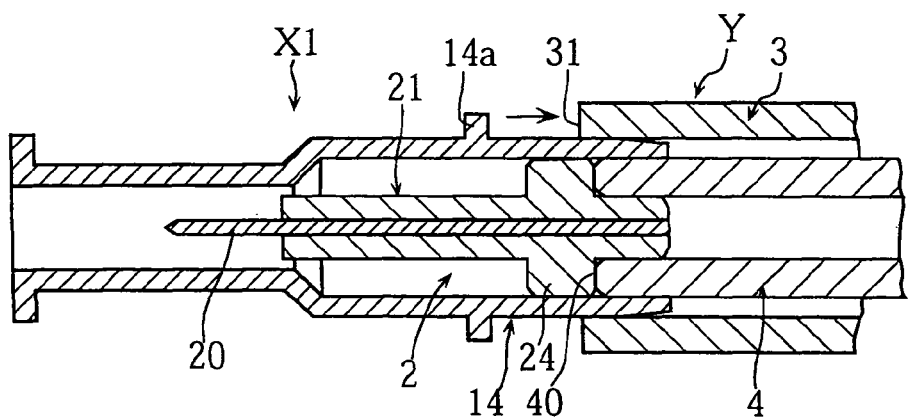
Figure 10C:
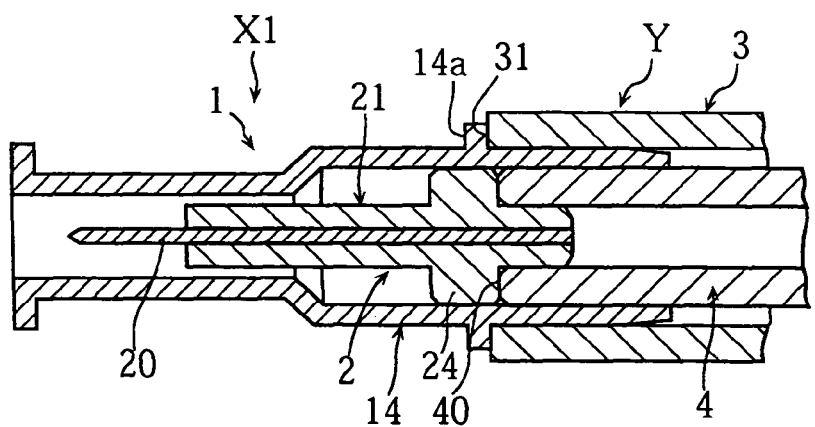
Figure 11A:
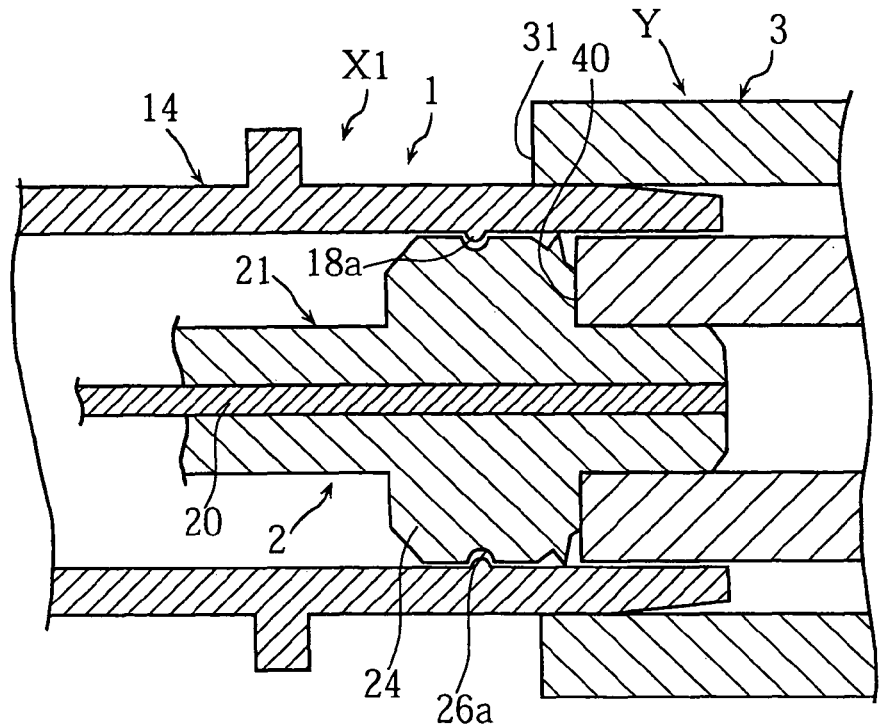
FIGS. 11A and 11B are enlarged sectional views of a principal portion for describing the work for mounting the lancet shown in FIG. 1 to a lancing apparatus.
Figure 11B:
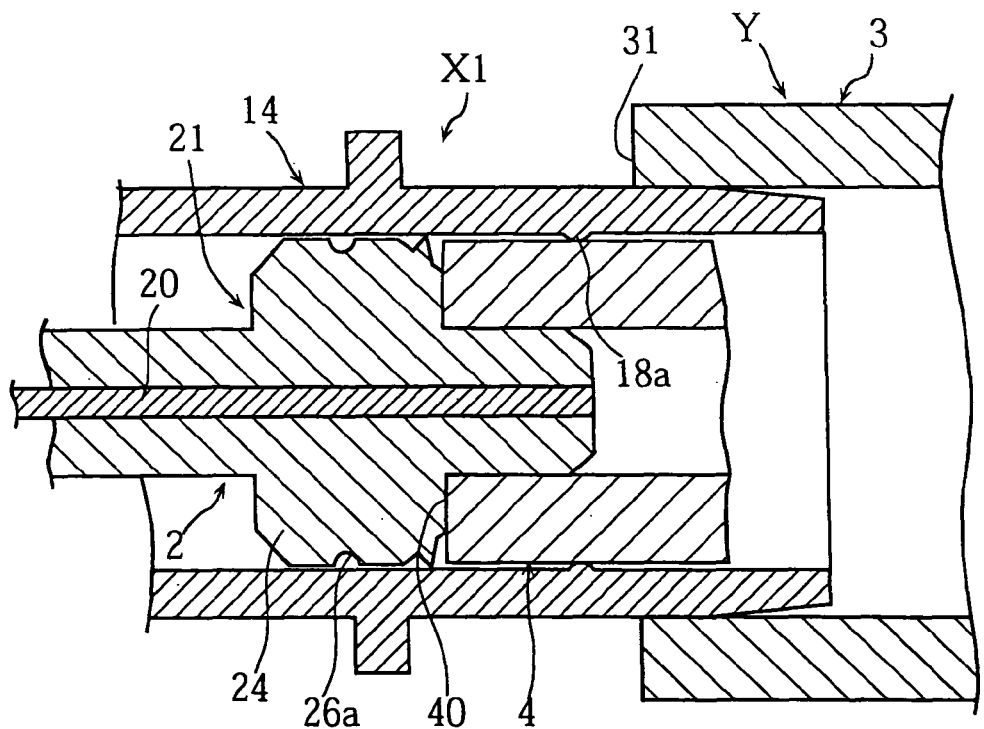

As shown in FIG. 10B, in inserting the lancet X1, an end surface 40 of the movable member 4 pushes the stopper 24 of the lancing unit 2. Until that time, the projections 18a of the case 1 is held in engagement with the annular recess 26a of the stopper 24, as shown in FIG. 11A. When the lancet X1 is inserted further from this state, the annular recess 26a disengages from the projections 18a due to the pushing force from the movable member 4 so that the lancing unit 2 moves in the advancing direction relative to the case 1, as shown in FIG. 11B. Since the flange 14a is formed on the outer surface of the case 1, the insertion of the lancet X1 is inhibited when the flange 14a interferes with the end surface 31 of the housing 3. Thus, the mounting of the lancet X1 to the lancing apparatus Y is completed.

Figure 12A:
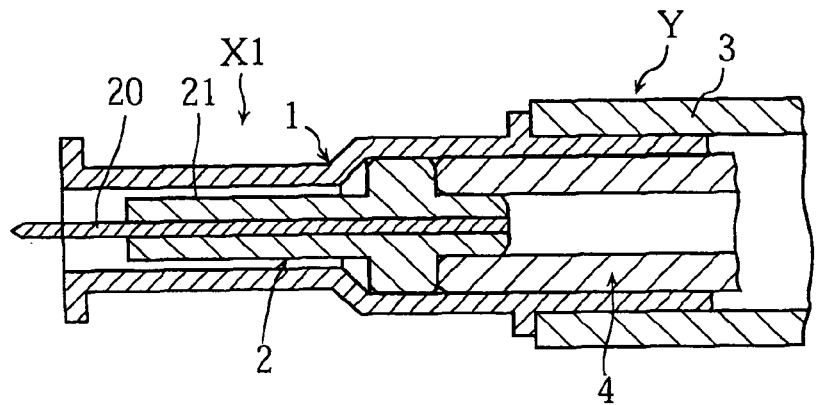
FIGS. 12A through 12C are sectional views for describing the lancing operation of the lancet shown in FIG. 1 and the work for detaching the lancet from the lancing apparatus.

As shown in FIG. 12A, in the lancing operation, the movable member 4 is moved in the advancing direction to move the lancing unit 2 in the advancing direction, thereby causing the lancing needle 20 to project from the case 1. Therefore, lancing of skin surface for bleeding can be performed by moving the movable member 4, with the case 1 pressed against the skin surface. This movement of the movable member 4 may be produced by exerting a resilient urging force on the movable member 4 held by a known latch mechanism and then releasing the latched state.

Figure 12B:
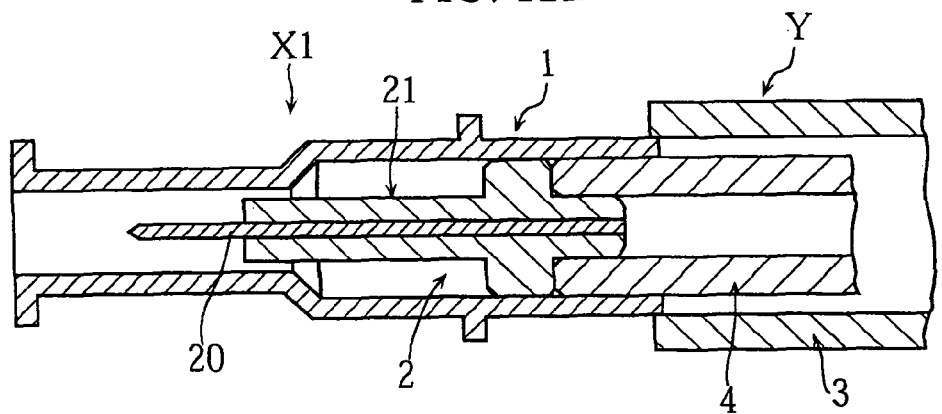
Figure 12C:
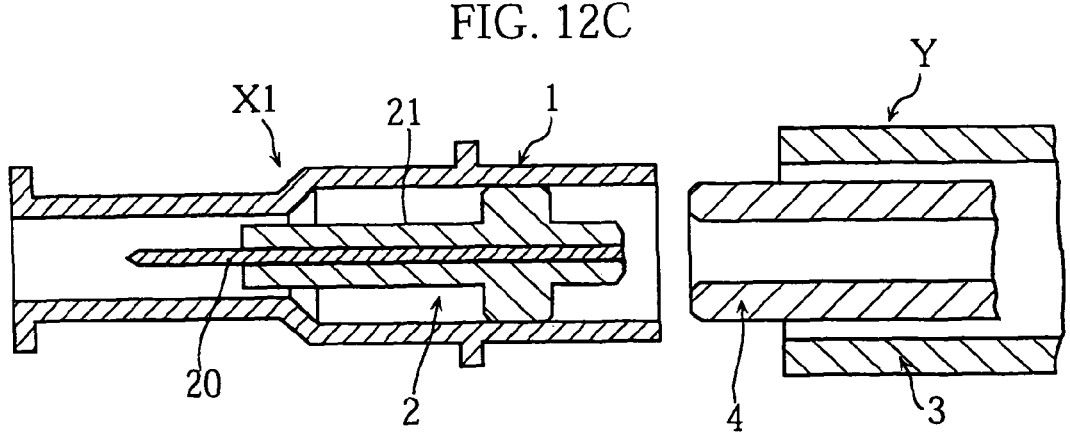
Figure 13:
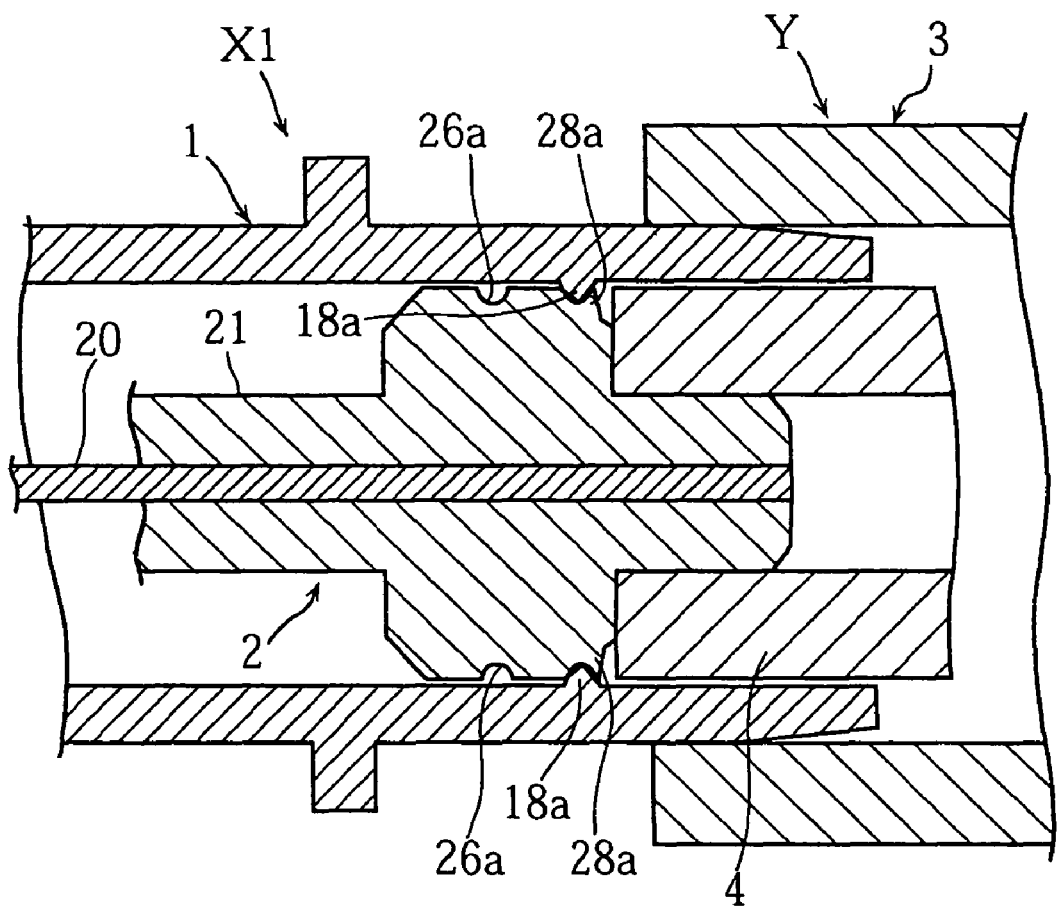
FIG. 13 is an enlarged sectional view of a principal portion for describing the work for detaching the lancet shown in FIG. 1 from the lancing apparatus.

After the lancing procedure is finished, the lancet X1 need be detached from the lancing apparatus Y. The detachment of the lancet X1 can be performed easily by moving the lancet X1 in the advancing direction relative to the lancing apparatus Y. At that time, since the rear end of the holder portion 21 of the lancing unit 2 is fitted in the movable member 4, the lancing unit 2 moves in the retreating direction relative to the case 1, as shown in FIG. 12B. The relative movement of the lancing unit 2 is performed until the projections 18a of the case 1 engage the projections 28a, as shown in FIG. 13. In the state in which the projections 28a engage the projections 18a, the lancing unit 2 is entirely accommodated in the case 1 so that the lancing needle 20 does not project from the case 1. This position corresponds to the wait position of the lancing unit 2. Thereafter, as shown in FIG. 12C, the case 1 moves together with the lancing unit 2, whereby the lancet X1 is detached form the lancing apparatus Y.

In the detaching operation of the lancet X1, the lancing unit 2 is retreated in the case 1 so that the lancing needle 20 does not project from the case 1. Further, the projections 18a are brought into engagement with the projections 28a. Therefore, in the detaching operation of the lancet X1, the lancing needle 20 is not kept projecting and the lancing unit 2 does not drop from the case 1, which is advantageous in ensuring safety and sanitation. Moreover, since the lancing needle 20 is prevented from projecting, it is not necessary to attach a cap for covering the lancing needle 20 in detaching the lancet X1. The elimination of the work for attaching the cap leads to enhancement in the operation efficiency.

Figure 14:
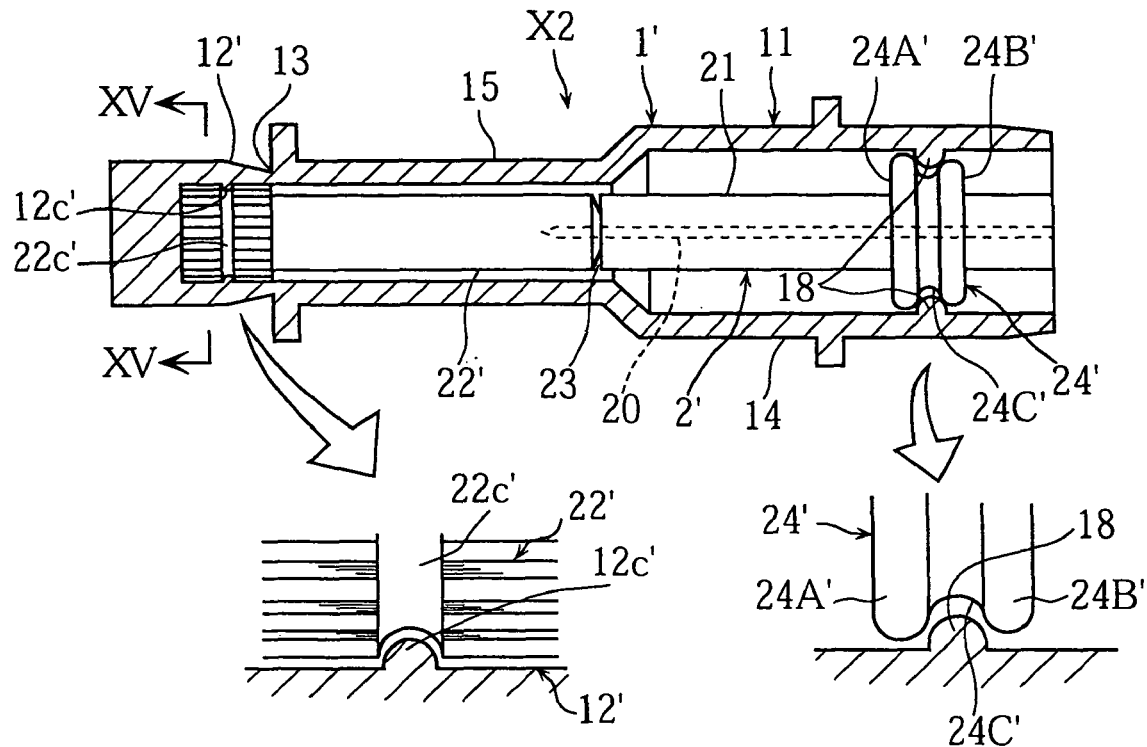
FIG. 14 is a sectional view of a lancet according to a second embodiment of the present invention, principal portions of which are illustrated as enlarged.
Figure 15:
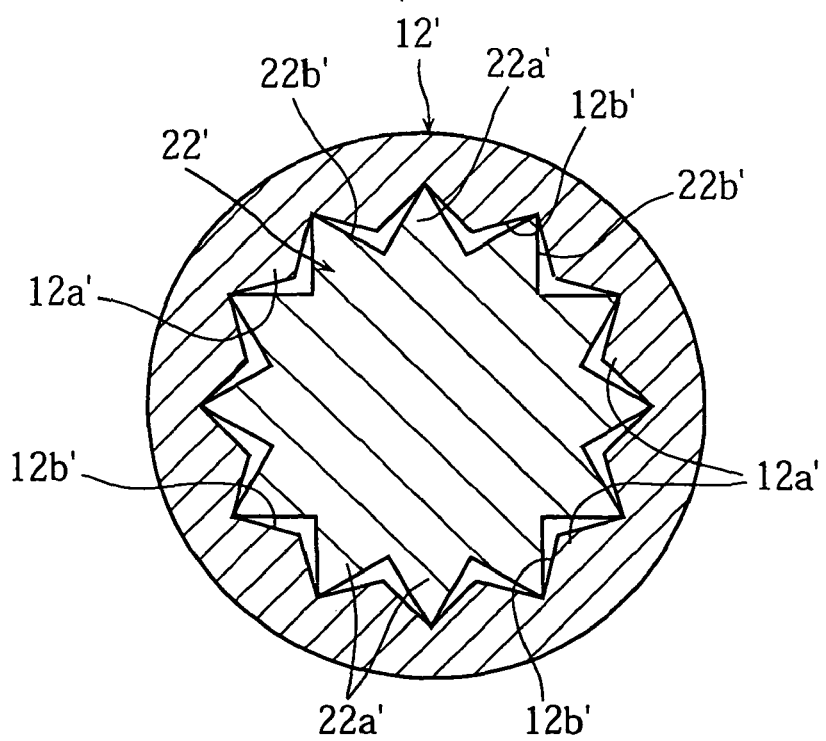
FIG. 15 is a sectional view taken along lines XV-XV in FIG. 14.

Next, a lancet X2 according to a second embodiment of the present invention will be described with reference to FIGS. 14 and 15. In these figures, the members or elements which are identical or similar to those of the lancet X1 of the first embodiment are designated by the same reference signs as those used in FIGS. 1 through 13, and the description thereof will be omitted.

The arrangements of the lancet X2 are basically similar to those of the above-described lancet X1 (See FIG. 1). However, the structure for moving the cover portion 22' of the lancing unit 2' together with the cap 12' of the case 1' is different, and so is the structure for holding the lancing unit 2' at the wait position or the retreated position in the case 1'.

In the lancet X2, the inner surface of the cap 12' and the outer surface of the front end of the cover portion 22' are provided with a plurality of axially-extending projections 12a', 22a' and recesses 12b', 22b' so that the cap 12' and the cover portion 22' move together in the rotational direction. Further, the inner surface of the cap 12' is provided with an annular projection or a plurality of projections 12c', while the outer surface of the front end of the cover portion 22' is provided with an annular projection 22c' for engagement with the annular projection or the plurality of projections 12c' With this structure, the cover portion 22' moves accompanying the movement of the cap 12' in the advancing/retreating direction. Alternatively, the cap 12' may be provided with an annular recess, while the cover portion 22' may be provided with an annular projection or a plurality of projections.

With the above structure again, the cover portion 22' can be detached together with the cap 12' by exerting a rotational force and a pulling force onto the cap 12'.

The stopper 24' of the lancing unit 2' comprises two circular flanges 24A' and 24B' aligned in the advancing/retreating direction. Between the flanges 24A' and 24B' is provided an annular recess 24C'. The front flange 24A' is larger in diameter than the rear flange 24B'.

With the above arrangement, the annular projection 18 of the case 1' engages the annular recess 24C' of the stopper 24 to hold the lancing unit 2' at the wait position. Further, when the lancing unit 2' is moved in the retreating direction relative to the case 1' after the lancing unit 2' is moved to the lancing position, the annular projection 18 of the case 1' can pass over the flange 24B' for fitting in the recess 24C', because the flange 24B' located on the retreating side has a smaller diameter. Since the flange 24A' has a larger diameter, the annular projection 18 cannot pass over the flange 24A' so that the engagement of the annular projection 18 with the recess 24C' is maintained. Therefore, in detaching the lancet X2 from the lancing apparatus, the lancing unit 2' is held in the case 1', with the lancing needle 20 prevented from projecting from the case.

With the lancet X2 again, the front end of the lancing needle 20 before use is covered with the cover portion 22, and therefore the manufacturing cost can be reduced. Further, after the lancing operation, the lancing unit 2 is held by the two circular flanges 24A' and 24B', so that the lancing needle 20 is prevented from projecting from the case 1.

Next, a lancet X3 according to a third embodiment of the present invention will be described with reference to FIGS. 16 and 17.

As shown in FIGS. 16 and 17, the lancet X3 differs from the above-described lancet X1 (See FIG. 1) in that the cap 12" is formed separately from the case 1.

The cap 12" has an inner surface formed with a plurality of projections 12a", while the cover portion 22" has an inner surface provided with a plurality of recesses 22a" for engagement with the projections 12a". With this arrangement, the cap 12" and the cover portion 22" can move together. Alternatively, the cap 12" may be provided with recesses while the cover portion 22" may be provided with projections for realizing the movement of the cover portion 22" together with the cap 12".

The above lancet X3 can also enjoy the advantages provided by covering the front end of the lancing needle 20 before use with the cover portion 22" and by providing the retaining means. The cover portion 22" can be detached easily by operating the cap 12".

In detaching the lancet X3, the lancing unit 2 may be held at the retreating position by a structure similar to that of the lancet X2.

Next, a lancet according to a fourth embodiment will be described with reference to FIGS. 18A through 18C.

Figure 18A:
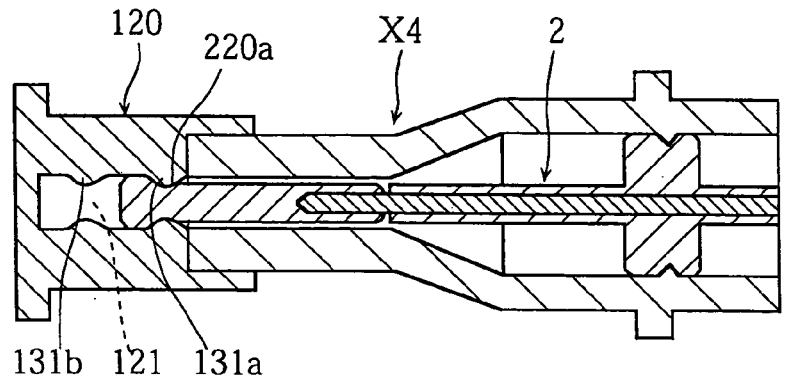
FIG. 18A through FIG. 18C are sectional views of a lancet according to a fourth embodiment of the present invention.

As shown in FIG. 18A, the arrangements of the lancet X4 are basically similar to those of the lancet X3 described with reference to FIG. 16, but the structure of a cap 120 is different from that of the lancet X3.

The cap 120 has a space 121 for receiving the front end of the lancing unit 2. The space 121 has a depth which is greater than the projecting amount of the cover portion 220 in the state when the lancing unit 2 is held at the wait position.

The cap 120 has an inner surface formed with a plurality of first projections 131a and a plurality of second projections 131b. Each of the first projections 131a engages a recess 220a of the cover portion 220 when the lancing unit 2 is held at the wait position. As shown in FIG. 18B, each of the second projections 131b engages the recess 220a of the cover portion 220 when the front end of the cover portion 220 is located at the deepest position in the space 121. When the first projection 131a or the second projection 131b engages with the recess 220a of the cover portion 220, the cover portion 220 can move together with the cap 120. As readily understood, the cap 120 may be provided with a recess whereas the cover portion 220 may be provided with a projection so that the cover portion 220 can move together with the cap 120.

Figure 18B:
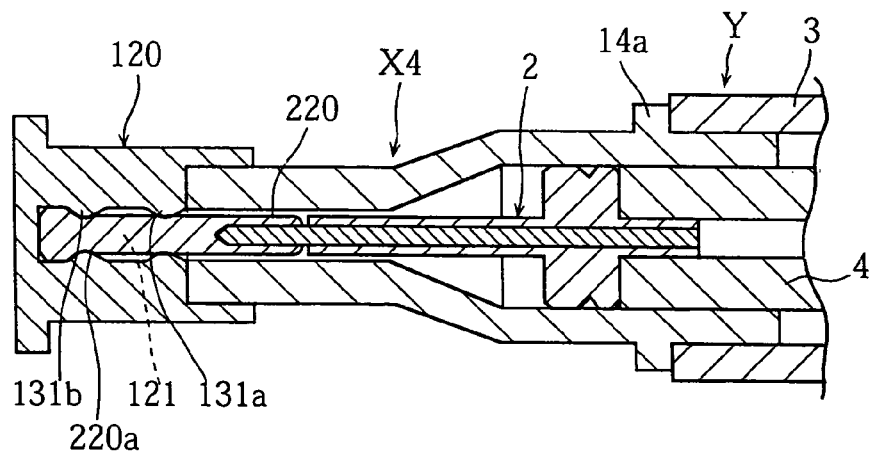
Figure 18C:
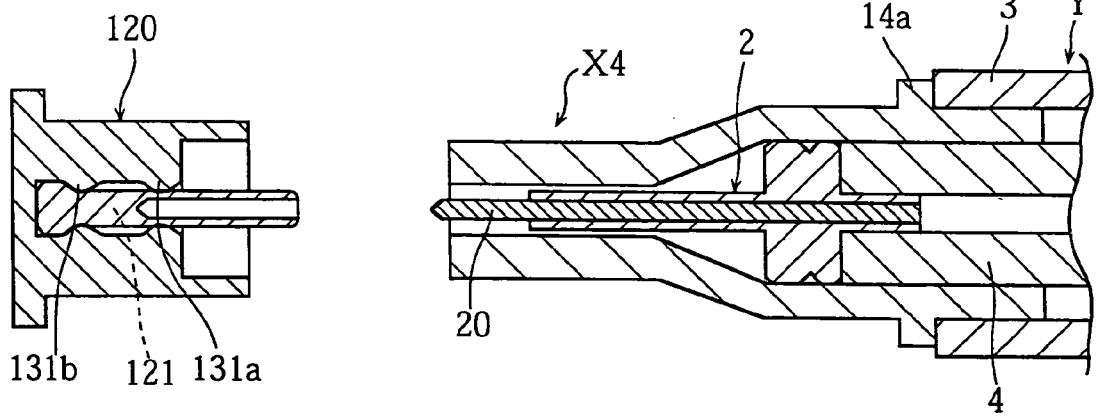

As shown in FIGS. 18B and 18C, in use the lancet X4 is mounted to a lancing apparatus Y which is similar to the assembly described in the first embodiment. In mounting the lancet X4, the rear end of the lancet X4 is inserted into the front end of the lancing apparatus Y. The insertion of the lancet X4 is continued until an end surface of the housing 3 comes into contact with a flange 14a. In this process, the lancing unit 2 moves in the forward direction of the lancet X4.

The cap 120 is removed before or after the lancet X4 is mounted. For this, the cap 120 is rotated while being pulled. In this process, the cover portion 220 is detached from the lancing unit 2. Thereafter, the movable member 4 is moved in the advancing direction, so that the lancing unit 2 is further moved in the advancing direction. Thus, the lancing needle 20 projects from the case 1, as shown in FIG. 18C. After the lancing operation is finished, the lancet X4 is detached from the lancing apparatus Y, as in the first embodiment. During this, the lancing unit 2 is entirely accommodated in the case 1, whereby the lancing needle 20 does not project from the case 1.

The cap 120 can be detached either before or after the lancet X4 is mounted to the lancing apparatus Y, which makes the lancet X4 a convenient tool.

Next, fifth through seventh embodiments will be described with reference to FIGS. 19 through 24. The lancets according to these embodiments are characterized by wait position holding means for holding the lancing unit at the wait position in the case. Thus, only the wait position holding means will be described below.

As shown in FIGS. 19, 20A and 20B, the wait position holding means 7A according to the fifth embodiment comprises a plurality of movable pieces 70A and a plurality of projections 70B provided on the case 1A, and a stopper 71A provided on the lancing unit 2A and having an annular recess 71a.

Each of the movable pieces 70A, around which a through-hole 70a is provided and which is made relatively thin, serves as a leaf spring. Each movable piece 70A has a front end provided with a projection 70b for stress concentration.

In the wait position holding means 7A, the stopper 71A is fixed to the case 1A due to the resilient force of the movable pieces 70A and the pressing force from the projections 70B. As a result, the lancing unit 2A is held at the wait position. In pulling out the lancet from the lancing apparatus after the lancing operation, the projection 70b of each movable piece 70A engages the annular recess 71a of the stopper 71A. Thus, the lancing unit 2A is held at the retreated position.

As shown in FIG. 21, the wait position holding means 7B according to the sixth embodiment differs from the wait position holding means 7A according to the fifth embodiment in the structure of the stopper of the lancing unit. The holding means 7B includes a stopper 71B which is similar in structure to the stopper 24' (See FIG. 14) of the lancing unit 2 according to the second embodiment.

The stopper 71B includes two circular flanges 71Ba and 71Bb which are different in diameter and aligned in the advancing/retreating direction. Between the flanges 71Ba and 71Bb is provided an annular recess 71Bc. The front flange 71Ba is larger in diameter than the rear flange 71Bb.

In the wait position holding means 7B, the front end of a movable piece 70B engages the annular recess 71Bc to hold the lancing unit 2B at the wait position. When the lancing unit 2B is moved in the retreating direction relative to the case 1B after the lancing unit 2B is moved to the lancing position, the front end of the movable piece 70B can pass over the flange 71Bb for fitting into the annular recess 71Bc, because the rear flange 71Bb has a smaller diameter. However, since the flange 71Ba has a larger diameter, the front end of the movable piece 70B cannot pass over the flange 71Ba, whereby the engagement of the front end of the movable piece 70B with the annular recess 71Bc is maintained.

As shown in FIGS. 22 through 24, the wait position holding means 7C according to the seventh embodiment includes a plurality of loop-like resilient portions 73C formed on the lancing unit 2C, and an annular projection 74C provided on the case 1C. Each of the resilient portions 73C is formed with a recess 73c.

In the wait position holding means 7C, the lancing unit 2C is held at the wait position in the case 1C due to the resilient force of the resilient members 73C. When the lancing unit 2C is moved in the retreating direction after the lancing operation, the annular projection 74C engages the recess 73c of each resilient member 73, thereby holding the lancing unit 2C at the retreated position in the case 1C.

Next, eighth and ninth embodiments will be described with reference to FIGS. 25 and 26. The lancets in these embodiments are characterized by retreated position holding means for fixing the lancing unit at the retreated position. Thus, only the retreated position holding means will be described below.

Figure 25A:
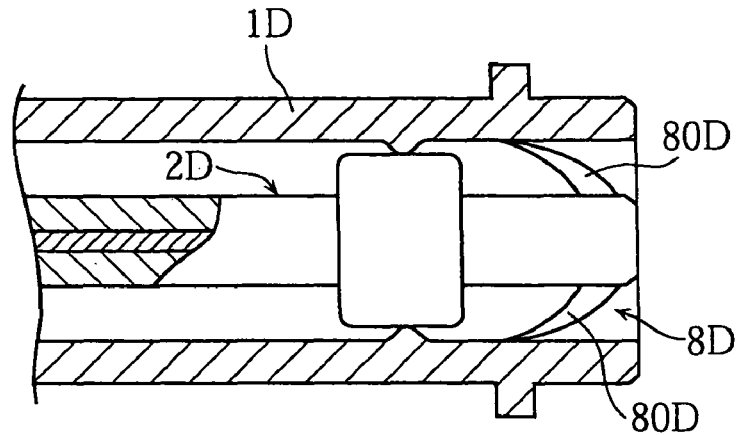

As shown in FIG. 25A, the retreated position holding means 8D according to the eighth embodiment includes a plurality of swayable members 80D provided on the lancing unit 2D.

Each of the swayable members 80D has a base end fixed to the lancing unit 2D and a front end which is movable toward and away from the lancing unit 2D. Each of the swayable members 80D is accommodated in the case 1D and biased outward. This condition may be realized by making the swayable member 80D as a leaf spring or interposing a resilient material between the swayable member 80D and the lancing unit 2D.

Figure 25B:
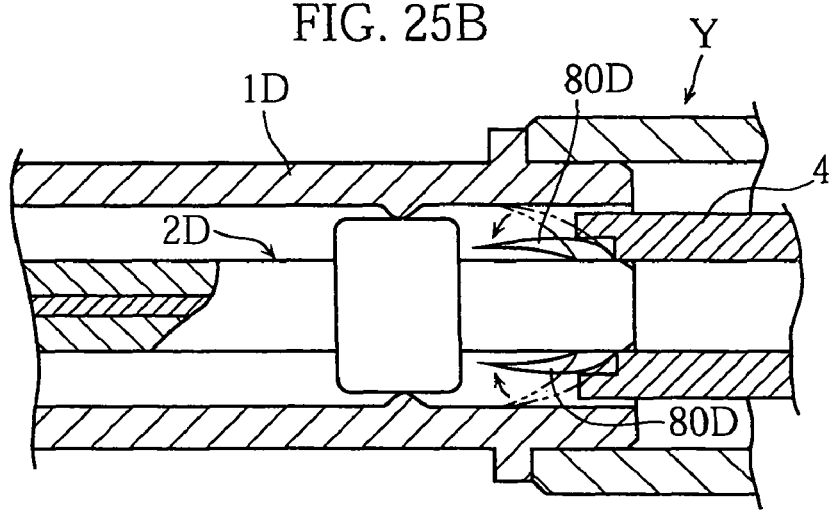

With the above arrangement, when the lancet is mounted to the lancing apparatus Y, each of the swayable members 80D is pushed inward by the movable member 4 to extend along the surface of the lancing unit 2D, as shown in FIG. 25B. Thus, when the lancing unit 2D is held at the wait position, each of the swayable members 80D does not interfere with the inner surface of the case 1D. This state is maintained as long as the lancet is fixed to the movable member 4. In this state, each of the swayable members 80D is biased outward of the lancing unit 2D.

Figure 25C:
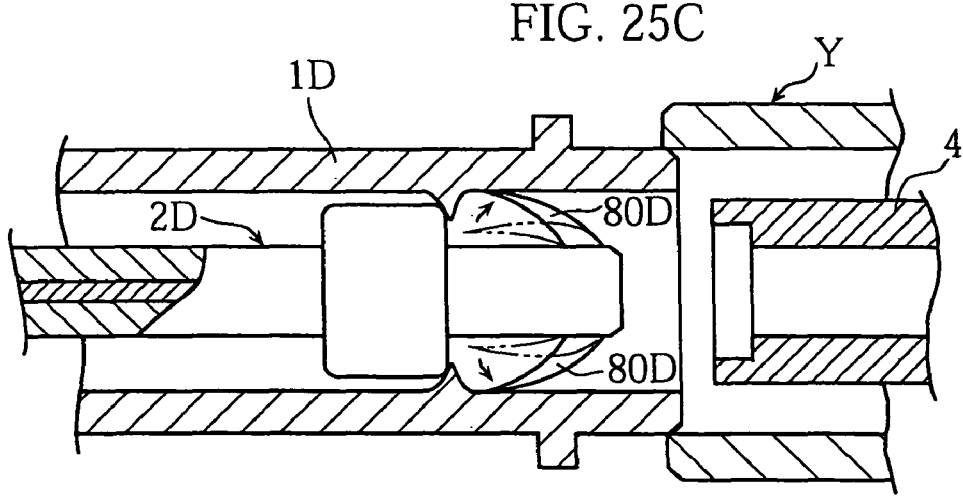

After the lancing operation is finished, the lancet is detached from the lancing apparatus. This allows each of the swayable members 80D to be released from the pushed state. Accordingly, as shown in FIG. 25C, the front end of the swayable member 80D moves outward. As a result, the front end of the swayable member 80D interferes with the inner surface of the case 1D, thereby holding the lancing unit 2D at the retreated position in the case 1D.

Figure 26A:
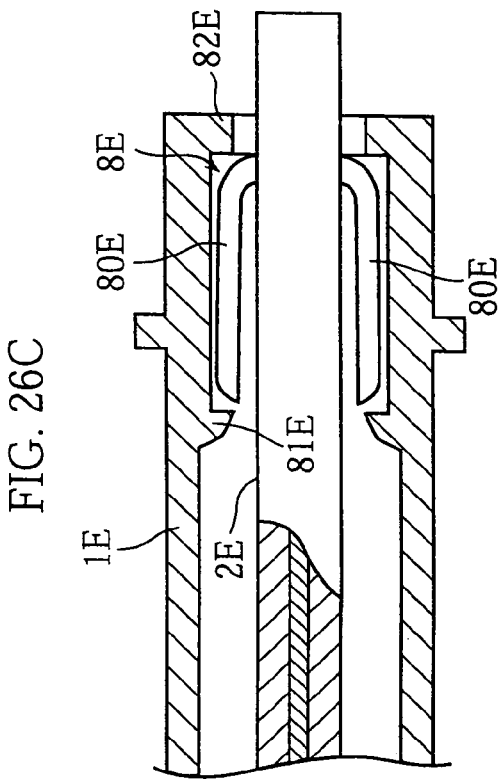
FIGS. 26A through 26D are perspective sectional views of a principal portion of a lancet according to a ninth embodiment of the present invention.

Referring to FIG. 26A, there treated position holding means 8E according to the ninth embodiment includes a plurality of swayable members 80E provided on the lancing unit 2E.

Each of the swayable members 80E is bent so that the front end thereof is oriented toward the front end of the lancet and accommodated in the case 1E while engaging the projection 81E, whereby the front end of the swayable member is located more inward than it is in the natural state. Thus, each of the swayable members 80E is held at the retreated position in the case 1E, with the resilient force tending to act toward the outside of the case 1E.

Figure 26B:
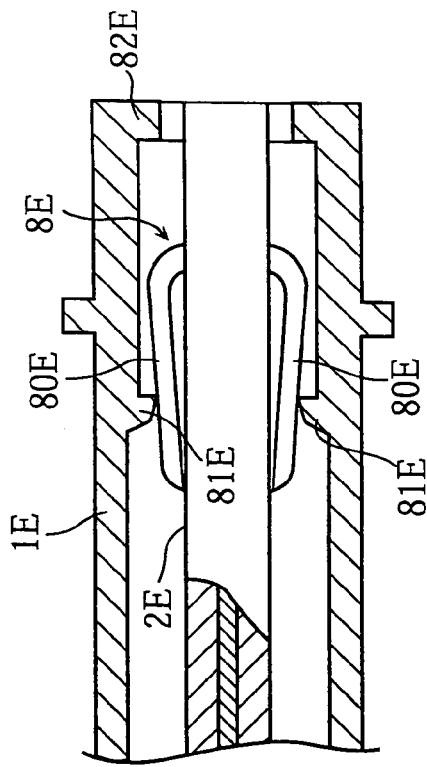

The case 1E is smaller in thickness on the advancing side of the projection 81E than on the retreating side of the projection 81E. Therefore, as shown in FIG. 26B, when the lancing unit 2E advances from the wait position to the lancing position, the swayable members 80E do not come into contact with the inner surface of the case 1E so that the lancing unit can move smoothly.

Figure 26C:
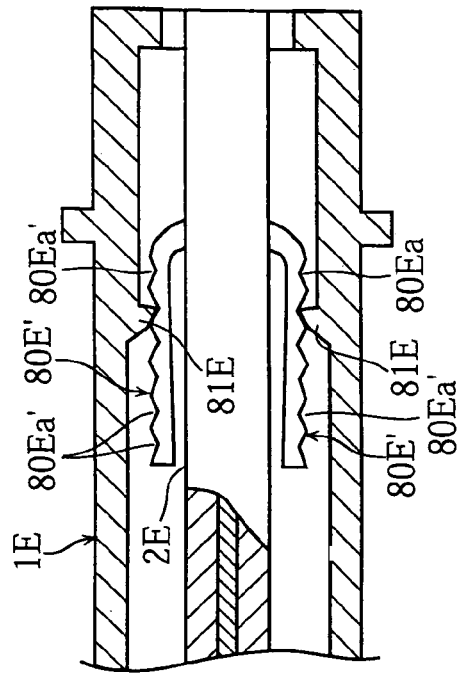

On the other hand, when the lancing unit 2E is moved toward the rear end of the lancet after the lancing operation, each of the swayable members 80E moves while exerting a resilient force onto the inner surface of the case 1, as shown in FIG. 26C. When the swayable members 80E interfere with the stopper 81E on the case 1E, the movement of the lancing unit 1E is inhibited at the retreated position, and the lancing unit 2E is held at the retreated position due to the resilient force of the swayable members 80E.

Figure 26D:
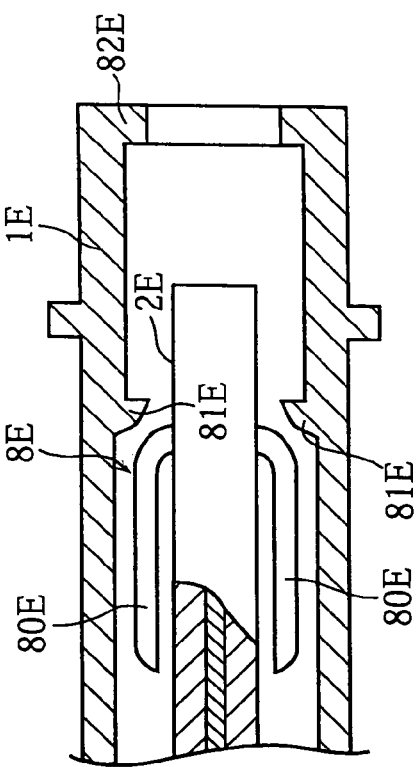
Figure 27A:
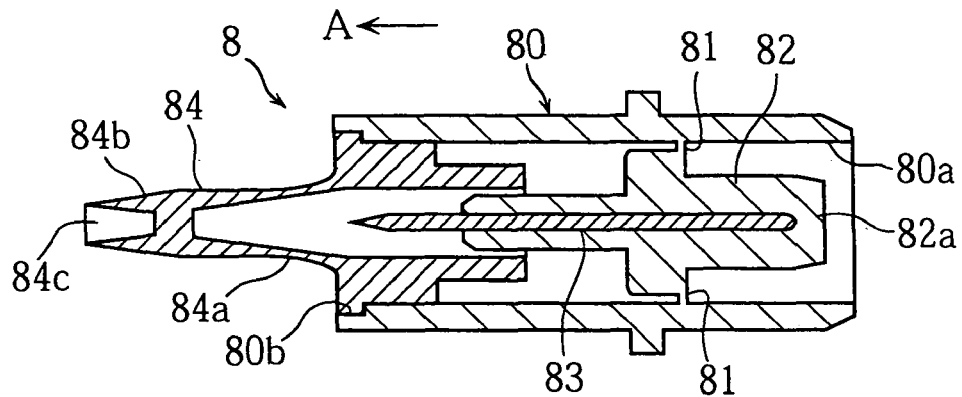
Figure 27B:
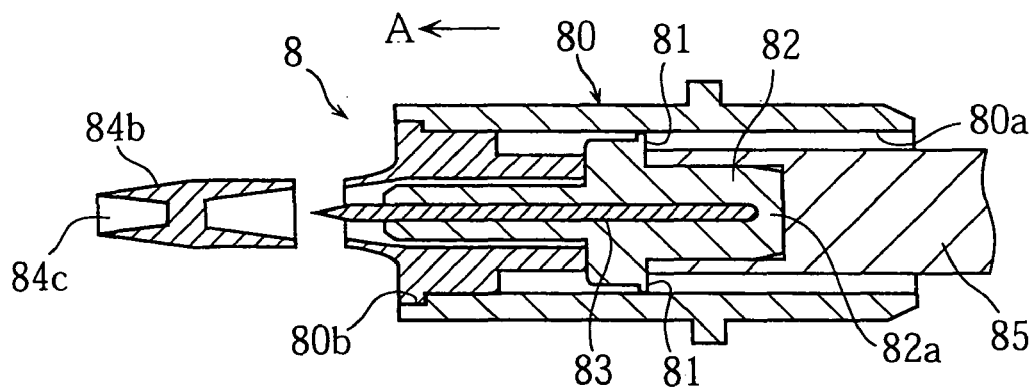
Figure 27C:
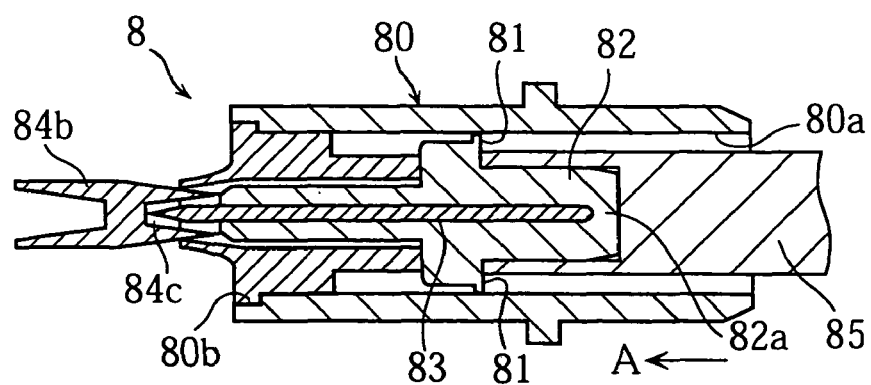
Figure 28A:
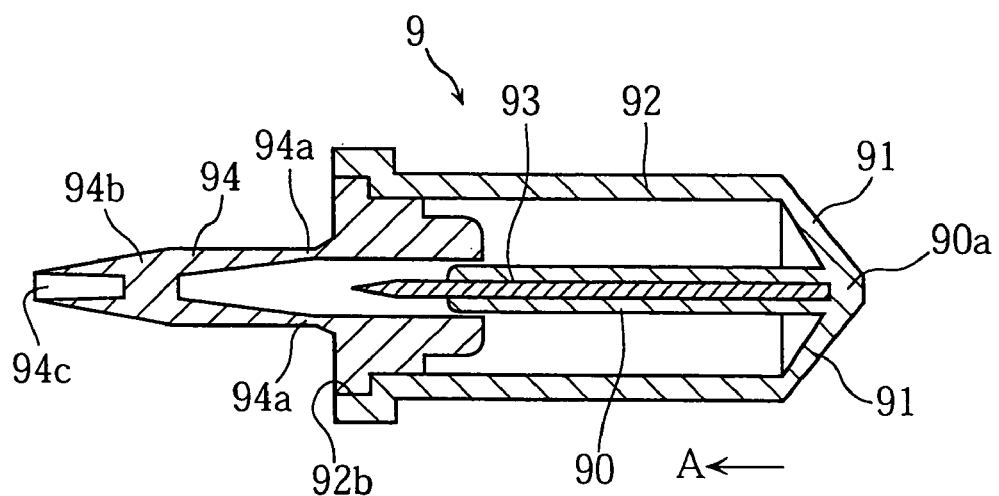
FIGS. 28A and 28B are sectional views illustrating another example of prior art lancet.
Figure 28B:
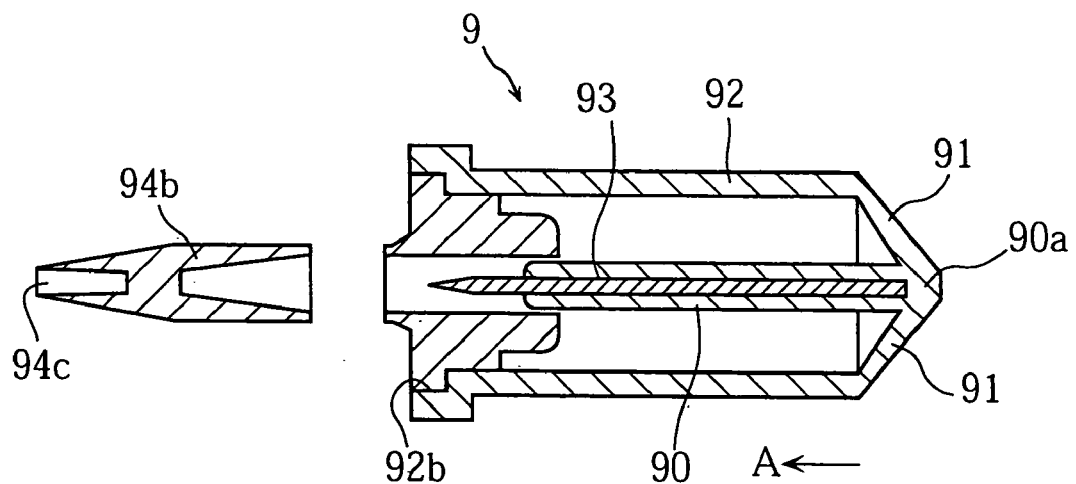

Referring to FIG. 26D, each swayable member 80E' may be formed with a plurality of successive recesses 80Ea' facing the case 1E. With this arrangement, the projection 81E of the case 1E engages the recess 80Ea' to hold the lancing unit 2E' at the wait position. As a result, the lancing unit 2E' can be held at the wait position more reliably. Though FIG. 26D shows a plurality of recesses 80Ea', only one recess may be sufficient.

The manner of constituting wait position holding means or the retreated position holding means by providing a resilient portion at the case or at the lancing unit is not limited to the examples described with reference to FIGS. 19 through 26.

The invention claimed is:

1. A lancet for attachment to a housing of a lancing apparatus, comprising:
  a case provided separately from the housing of the lancing apparatus and including an internal space, and a lancing unit including a lancing needle and movable within the internal space in an advancing direction from a wait position to an advanced position;
  wherein the case comprises a main body accommodating the lancing unit and having a tubular mounting portion for removable attachment to the housing of the lancing apparatus, and a cap directly connected to the main body, the cap being detachable from the main body;
  wherein the lancing unit comprises a cover portion for covering a front end of the lancing needle, the cover portion being initially separate from the cap, the cover portion being brought into engagement with the cap;
  wherein the cover portion is detached from the lancing needle together with detachment of the cap from the main body for exposing the front end of the lancing needle; and
  wherein the main body keeps accommodating the lancing unit before attachment of the main body to the housing of the lancing apparatus and after removal of the main body from the housing of the lancing apparatus.

2. The lancet according to claim 1, wherein the lancing unit comprises:
  a holder portion for holding a portion of the lancing needle opposite to the front end.

3. The lancet according to claim 2, further comprising rotational means for rotating the cover portion in accordance with rotation of the cap;
  wherein the cover portion is detached from the lancing needle together with the cap by exerting a rotational force for rotating the cap and a pulling force for causing relative movement of the cap in the advancing direction.

4. The lancet according to claim 3, wherein the rotational means comprises:
  an engagement piece which is provided on the cover portion and has a front end movable in a direction transverse to the advancing direction of the lancing unit; and
  an engagement counterpart provided at the cap for engagement with the engagement piece for restraining the front end of the engagement piece in the rotational direction and in the advancing direction.

5. The lancet according to claim 3, wherein the rotational means comprises a recess or a projection provided on the cover portion, and a projection or a recess provided on the cap for engagement with the recess or the projection of the cover portion.

6. The lancet according to claim 3, further comprising rotation preventing means for preventing the holder portion from rotating when the cap is rotated.

7. The lancet according to claim 1, further comprising wait position holding means for holding the lancing unit at the wait position; wherein the wait position holding means includes a resilient portion provided on at least one of the case and the lancing unit, the lancing unit being held in place by a spring force of the resilient portion.

8. The lancet according to claim 1, further comprising retreated position holding means for holding the lancing unit at a retreated position after the lancing unit is retreated from the advanced position to the retreated position upon removal of the case from the housing of the lancing apparatus.

9. The lancet according to claim 1, wherein the cap is integrally formed with the main body as one piece.

10. A lancet for attachment to a housing of a lancing apparatus, comprising:
  a case provided separately from the housing of the lancing apparatus and including an internal space, and a lancing unit including a lancing needle and movable within the internal space in an advancing direction from a wait position to an advanced position;
  wherein the case comprises a main body which accommodates the lancing unit and has a rear opening for inserting the lancing needle, and a cap directly connected to a front end of the main body, the cap being detachable from the front end of the main body;
  wherein the lancing unit comprises a holder portion for holding a portion of the lancing needle on a retreating side, and a cover portion for covering a portion of the lancing needle on an advancing side, the cover portion being detachable from the holder portion, the cover portion being initially separate from the cap, the cover portion being brought into engagement with the cap;
  wherein the cover portion is detached from the lancing needle together with detachment of the cap from the front end of the main body for exposing a front end of the lancing needle, without causing the lancing needle to project beyond the front end of the main body; and
  wherein the main body keeps accommodating the lancing unit before attachment of the main body to the housing of the lancing apparatus and after removal of the main body from the housing of the lancing apparatus.

11. The lancet according to claim 10, further comprising rotational means for rotating the cover portion in accordance with rotation of the cap,
  wherein the cover portion is detached together with the cap by exerting a rotational force for rotating the cap and a pulling force for causing relative movement of the cap in the advancing direction.

12. The lancet according to claim 11, wherein the rotational means comprises:

an engagement piece provided at the cover portion and having a front end movable in a direction transverse to the advancing direction of the lancing unit; and an engagement counterpart provided at the cap for engagement with the engagement piece for restraining the front end of the engagement piece in the rotational direction and the advancing direction.

13. The lancet according to claim 11, wherein the rotational means comprises:

a recess or a projection provided at the cover portion; and a projection or a recess provided at the cap for engagement with the recess or the projection of the cover portion.

14. The lancet according to claim 11, further comprising rotation preventing means for preventing the holder portion from rotating when the cap is rotated.

15. The lancet according to claim 10, further comprising a weak portion for detachably connecting the cap and the main body.

16. The lancet according to claim 10, further comprising a weak portion for detachably connecting the holder portion and the cover portion.

17. The lancet according to claim 10, wherein the cap is integrally formed with the main body as one piece.

18. A lancet for attachment to a housing of a lancing apparatus, comprising:

a case provided separately from the housing of the lancing apparatus and including an internal space, and a lancing unit including a lancing needle and movable within the internal space in an advancing direction from a wait position to an advanced position;

wherein the case comprises a main body accommodating the lancing unit, and a cap directly connected to the main body, the cap being detachable from the main body;

wherein the lancing unit comprises a cover portion for covering a front end of the lancing needle, the cover portion being initially separate from the cap, the cover portion being brought into engagement with the cap;

wherein the cover portion is detached from the lancing needle together with detachment of the cap from the main body for exposing the front end of the lancing needle;

wherein the main body of the case is removable from the housing of the lancing apparatus together with the lancing unit from which the cover portion has been detached; and wherein the main body keeps accommodating the lancing unit before attachment of the main body to the housing of the lancing apparatus and after removal of the main body from the housing of the lancing apparatus.

19. A lancet for attachment to a housing of a lancing apparatus, comprising:

a case provided separately from the housing of the lancing apparatus and including an internal space, and a lancing unit including a lancing needle and movable within the internal space in an advancing direction from a wait position to an advanced position;

wherein the case comprises a main body accommodating the lancing unit and having a tubular mounting portion for removable attachment to the housing of the lancing apparatus, and a cap directly connected to the main body, the cap being detachable from the main body;

wherein the lancing unit comprises a cover portion for covering a front end of the lancing needle, the cover portion being initially separate from the cap, the cover portion being brought into engagement with the cap;

wherein the cover portion is detached from the lancing needle together with detachment of the cap from the main body for exposing the front end of the lancing needle; and wherein the main body of the case contacts a portion of the lancing unit that is closer to a rear end of the lancing unit than it is to a lancing tip of the lancing needle.

20. The lancet according to claim 19, further comprising wait position holding means for holding the lancing unit at the wait position;

wherein the wait position holding means includes a resilient portion provided on at least one of the case and the lancing unit, the lancing unit being held in place by a spring force of the resilient portion.

21. The lancet according to claim 20, further comprising retreated position holding means for holding the lancing unit at a retreated position after the lancing unit is retreated from the advanced position to the retreated position upon removal of the case from the housing of the lancing apparatus, the retreated position and the wait position being different from each other axially of the lancing needle.

22. The lancet according to claim 19, further comprising retreated position holding means for holding the lancing unit at a retreated position after the lancing unit is retreated from the advanced position to the retreated position upon removal of the case from the housing of the lancing apparatus.

* * * * *